(12) United States Patent
Suzuki et al.

(10) Patent No.: US 8,113,034 B2
(45) Date of Patent: Feb. 14, 2012

(54) GAS SENSOR WITH PIPING FOR THE INTRODUCTION OF INSPECTION GAS

(75) Inventors: Akihiro Suzuki, Saitama (JP); Takashi Sasaki, Saitama (JP); Hideharu Naito, Saitama (JP); Kotaro Shigeno, Saitama (JP)

(73) Assignee: Honda Motor Co., Ltd., Tokyo (JP)

( * ) Notice: Subject to any disclaimer, the term of this patent is extended or adjusted under 35 U.S.C. 154(b) by 628 days.

(21) Appl. No.: 12/249,490

(22) Filed: Oct. 10, 2008

(65) Prior Publication Data

US 2009/0095051 A1   Apr. 16, 2009

(30) Foreign Application Priority Data

Oct. 12, 2007   (JP) ................................. 2007-266493
Jun. 19, 2008   (JP) ................................. 2008-160909
Aug. 5, 2008   (JP) ................................. 2008-201932

(51) Int. Cl.
*G01N 7/00* (2006.01)
*H01M 8/00* (2006.01)

(52) U.S. Cl. ........................................ 73/23.2; 429/400
(58) Field of Classification Search ................... 429/400
See application file for complete search history.

(56) References Cited

U.S. PATENT DOCUMENTS 4,738,147 A * 4/1988 Tomlin ...................... 73/864.81

FOREIGN PATENT DOCUMENTS

| JP | 2005-202623 A | | 7/2005 |
|---|---|---|---|
| JP | 2006-329786 A | | 7/2006 |
| JP | 2006-329786 A | * | 7/2006 |
| JP | 2007-20238 A | | 1/2007 |

* cited by examiner

*Primary Examiner* — Hezron E Williams
*Assistant Examiner* — Nathaniel Kolb
(74) *Attorney, Agent, or Firm* — Westerman, Hattori, Daniels & Adrian, LLP

(57) ABSTRACT

An apparatus includes a gas sensor configured to detect a specific gas which is a subject for detection, and inspection gas introduction piping configured to lead an inspection gas to the gas sensor, wherein at least a portion of the inspection gas introduction piping serves as ventilating piping configured to ventilate an inside of a ventilation-requiring device.

14 Claims, 16 Drawing Sheets

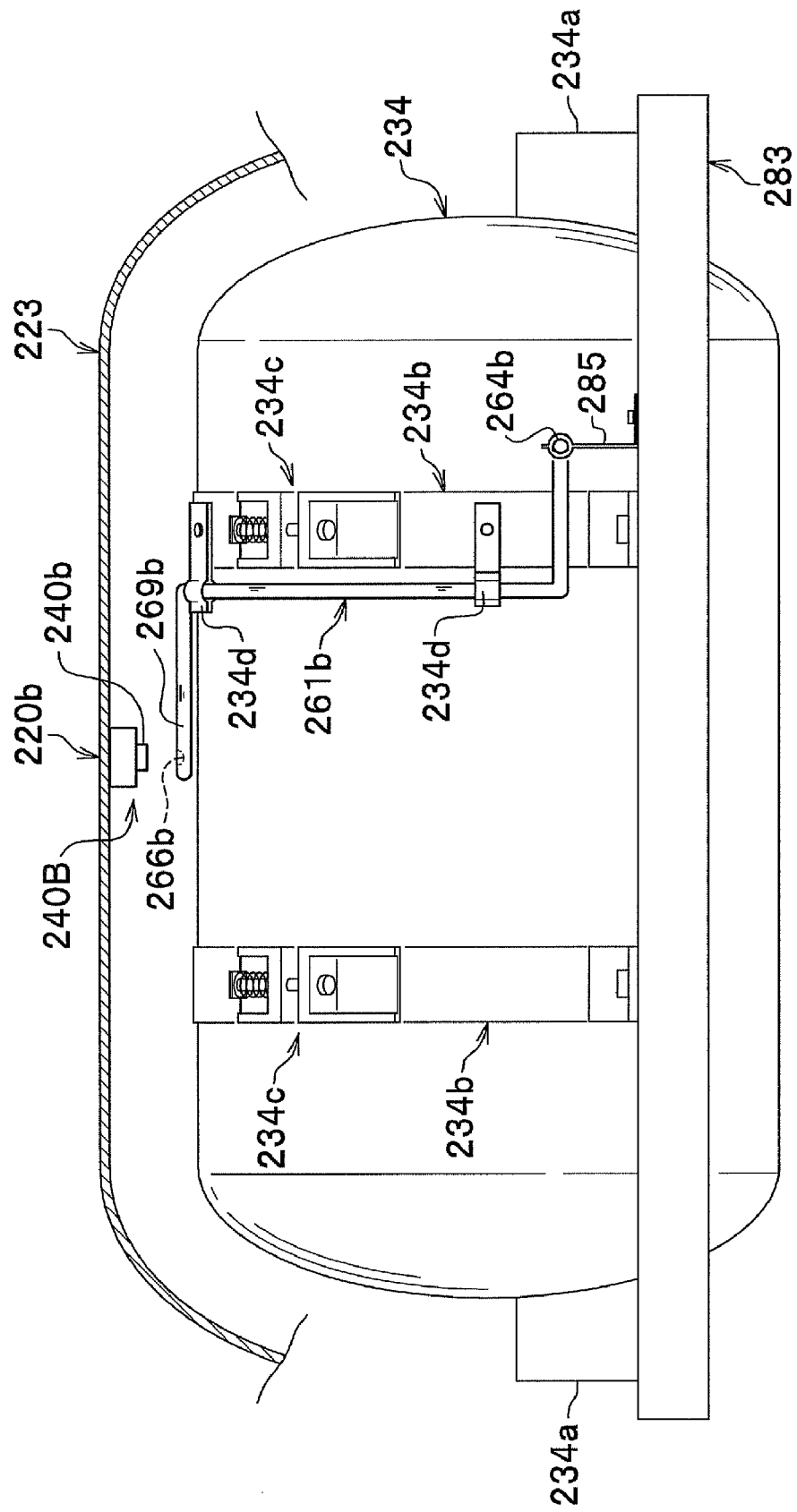

GAS SENSOR WITH PIPING FOR THE INTRODUCTION OF INSPECTION GAS

CROSS-REFERENCE TO RELATED APPLICATIONS

This application claims the foreign priority benefit under Title 35, United States Code, section 119 (a)-(d), of Japanese Patent Applications No. 2007-266493 filed on Oct. 12, 2007, No. 2008-160909 filed on Jun. 19, 2008 and No. 2008-201932 filed on Aug. 5, 2008 in the Japan Patent Office, the disclosures of which are herein incorporated by reference in their entirety.

BACKGROUND OF THE INVENTION

1. Field of the Invention

The present invention relates to an apparatus with a gas sensor. The present invention especially relates to an apparatus with a gas sensor used for a fuel cell system driven by power from a fuel cell, specifically a fuel cell vehicle.

2. Description of the Related Art

Conventionally, there has been known a gas alarm including a gas tight housing having an inside channel and an inspection gas channel communicating the inside channel, in which an inspection gas is supplied to an inspection gas introduction part and then ejected from a nozzle of the inspection gas introduction part to the inspection gas channel, and therethrough reaches a gas sensor element disposed in the inside channel (see, for example, JP2005-202623A).

Such a structure is introduced to a fuel cell vehicle. The fuel cell vehicle is provided with a solid polymer type fuel-cell stack and a hydrogen tank under, for example, a floor panel, and with a hydrogen sensor configured to detect hydrogen leakage. Since hydrogen has a smaller specific gravity than that of air, the hydrogen sensor should be placed above the fuel cell system. In other words, the hydrogen sensor is attached to a lower face of the floor panel, which is above the hydrogen tank and the fuel cell. As a result, the hydrogen sensor is placed at a position where it is difficult to visually check the hydrogen sensor from outside the vehicle, and to access with hands or tools. Therefore, during maintenance of the vehicle, when the hydrogen sensor is to be inspected by spraying an inspection gas, there arises a problem of removing a part of components from the vehicle, leading to more complicated inspection work.

In order to solve this problem, there has been proposed a technique in which the inspection work is made facilitated by attaching piping to the vehicle in advance, which is configured to lead an inspection gas (calibration gas) to a vicinity of the hydrogen sensor from a distant position (see, for example, JP2006-329786A).

On the other hand, the fuel cell vehicle mounts various electric power devices configured to control high power, so as to obtain a driving force from a high-output motor. In addition, in order to prevent internal short-circuit (electrical short), the electric power device is encased in a sealed container for protecting from intrusion of foreign matters, such as water and debris. In the sealed container, a vent hole communicating with the atmosphere is formed, in order to prevent inner pressure fluctuation which may be caused along with the generation of Joule heat (see, for example, JP2007-20238A).

In addition, in the case where this electric power device is positioned under the vehicle interior, the electric power device directly suffers splash of water, mud, debris and the like from the road surface during vehicle running, and therefore it is desired that the vent hole be positioned as high as possible. Accordingly, in order to prevent the splashed water, mud, debris and the like from entering the electric power device, it would be suggested that a breathing pipe which communicates with the sealed container, extends upward and has an upper end serving as a vent hole, be provided.

In the above-mentioned prior art gas alarm, it is necessary to include the inspection gas channel specially designed for passing an inspection gas, and the inspection gas introduction part specially designed for ejecting the inspection gas into the inspection gas channel. Further, in the fuel cell vehicle, in addition to the piping for these channels, it is necessary to install vent piping for the electric power device, leading to a problem that the structure of the fuel cell system becomes complicated and larger.

With respect to the vent piping for the electric power device, if droplets attach and accumulate inside the vent piping due to condensation or the like, water may flow to the electric power device or clog the breathing piping, which may deteriorate the prevention mechanism of the inner pressure fluctuation. Accordingly, in order to secure a performance stability of the electric power device, the breathing piping should be periodically cleaned, which lowers maintainability of the fuel cell vehicle.

Moreover, when such a hydrogen sensor is to be replaced, not only the hydrogen tank or the fuel cell stack locating thereunder should be removed, but also the inspection gas introduction piping, which requires longer working hours.

Therefore, it would be desirable to provide an apparatus which enhances efficiency of installing piping for supplying an inspection gas to the sensing element. It would be also desirable to provide an apparatus used for a fuel cell system which enhances performance stability of the electric power device and maintainability of the fuel cell system. It would be further desirable to provide an apparatus used for a fuel cell system having the inspection gas introduction piping, which improves workability in gas sensor exchange or the like.

SUMMARY OF THE INVENTION

In one aspect of the present invention, there is provided an apparatus including: a gas sensor configured to detect a specific gas which is a subject for detection, and inspection gas introduction piping configured to lead an inspection gas to the gas sensor, wherein at least a portion of the inspection gas introduction piping serves as ventilating piping configured to ventilate an inside of a ventilation-requiring device.

In the apparatus as described above, it is preferable that it is used for a fuel cell system including: a fuel cell configured to generate electricity with a fuel gas and an oxidant gas supplied thereto, a fuel gas container configured to contain a fuel gas therein, and an electric power device as the ventilation-requiring device configured to perform a power control of the fuel cell system and encased in a sealed container having a vent hole, the apparatus including: a fuel gas holding portion configured to surround an upper portion of the fuel gas container, a gas sensor including a gas sensing part having a downward opening, configured to be installed in the fuel gas holding portion and to detect a fuel gas staying in the fuel gas holding portion, first piping as the inspection gas introduction piping configured to, upon inspecting the gas sensor, lead an inspection gas to the gas sensor and to spray the inspection gas onto the gas sensing part from an end portion of the first piping, and second piping which includes a channel communicating with the sealed container and extending from the vent hole, wherein at least a portion of the first piping connected to the second piping serves as the ventilating piping for the electric power device.

In the apparatus as described above, it is preferable that the channel of the second piping extending from the vent hole is detachably connected to the first piping.

In the apparatus as described above, it is preferable that it is used for a fuel cell system including: a fuel cell configured to generate electricity with a fuel gas and an oxidant gas supplied thereto, and a fuel gas container configured to contain a fuel gas therein, the apparatus including: a fuel gas holding portion configured to surround an upper portion of the fuel gas container, a gas sensor including a gas sensing part having a downward opening, configured to be installed in the fuel gas holding portion and to detect a fuel gas staying in the fuel gas holding portion, and the inspection gas introduction piping configured to, upon inspecting the gas sensor, lead an inspection gas to the gas sensor and to spray the inspection gas onto the gas sensing part from an end portion of the inspection gas introduction piping, wherein the inspection gas introduction piping is fixed to the fuel gas container.

BRIEF DESCRIPTION OF THE DRAWINGS

The various aspects, other advantages and further features of the present invention will become more apparent by describing in detail illustrative, non-limiting embodiments thereof with reference to the accompanying drawings.

FIG. 24 is a front view showing the fuel tank and surrounding portions according to the modified version of the third embodiment.

DETAILED DESCRIPTION OF PREFERRED EMBODIMENTS

Embodiments of the present invention will be described in detail below with reference to the accompanying drawings.

First Embodiment

In a first embodiment, an apparatus with a gas sensor is briefly explained as an apparatus used for a fuel cell system.

Figure 1:
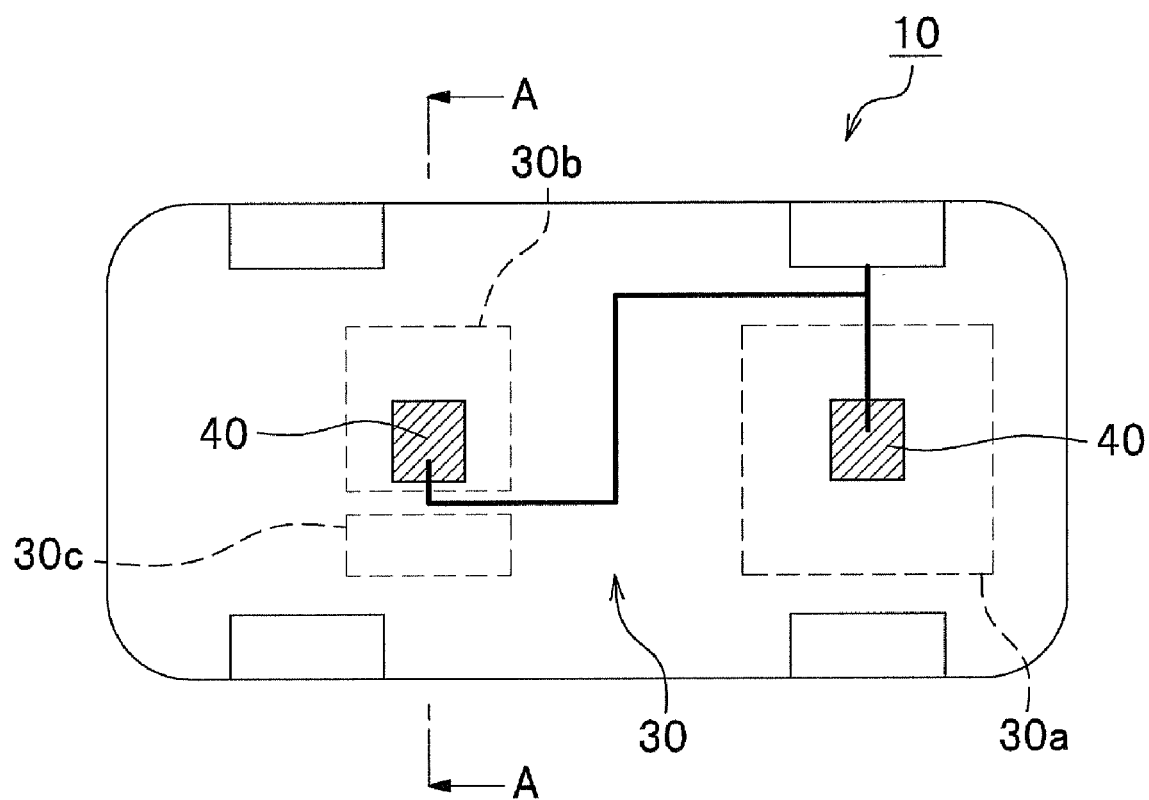
FIG. 1 is a plan view showing a main portion of an apparatus (fuel cell system) having a gas sensor according to a first embodiment of the present invention seen from below a vehicle body.

An apparatus 1 having a gas sensor (gas sensor-equipped apparatus 1) according to this embodiment is, for example as shown in FIG. 1, a fuel cell system 30 mounted on a fuel cell vehicle or an electric-motor vehicle 10, as a power source for the vehicle 10. For example, the fuel cell system 30 includes: a solid polymer electrolyte type fuel cell; a fuel supply unit having a fuel tank configured to store a hydrogen gas as a fuel gas, a regulator and the like; an air supply unit having a supercharger or the like configured to supply air containing oxygen as an oxidant gas to the fuel cell; a current controller configured to control a current generated by the fuel cell; various fuel cell devices 30a, 30b, 30c, . . . including an electric storage device or the like, e.g., capacitor configured to store power generated by the fuel cell; and a gas sensor 40 of, for example catalytic combustion type or semiconductor type, configured to detect a hydrogen gas.

Figure 2:
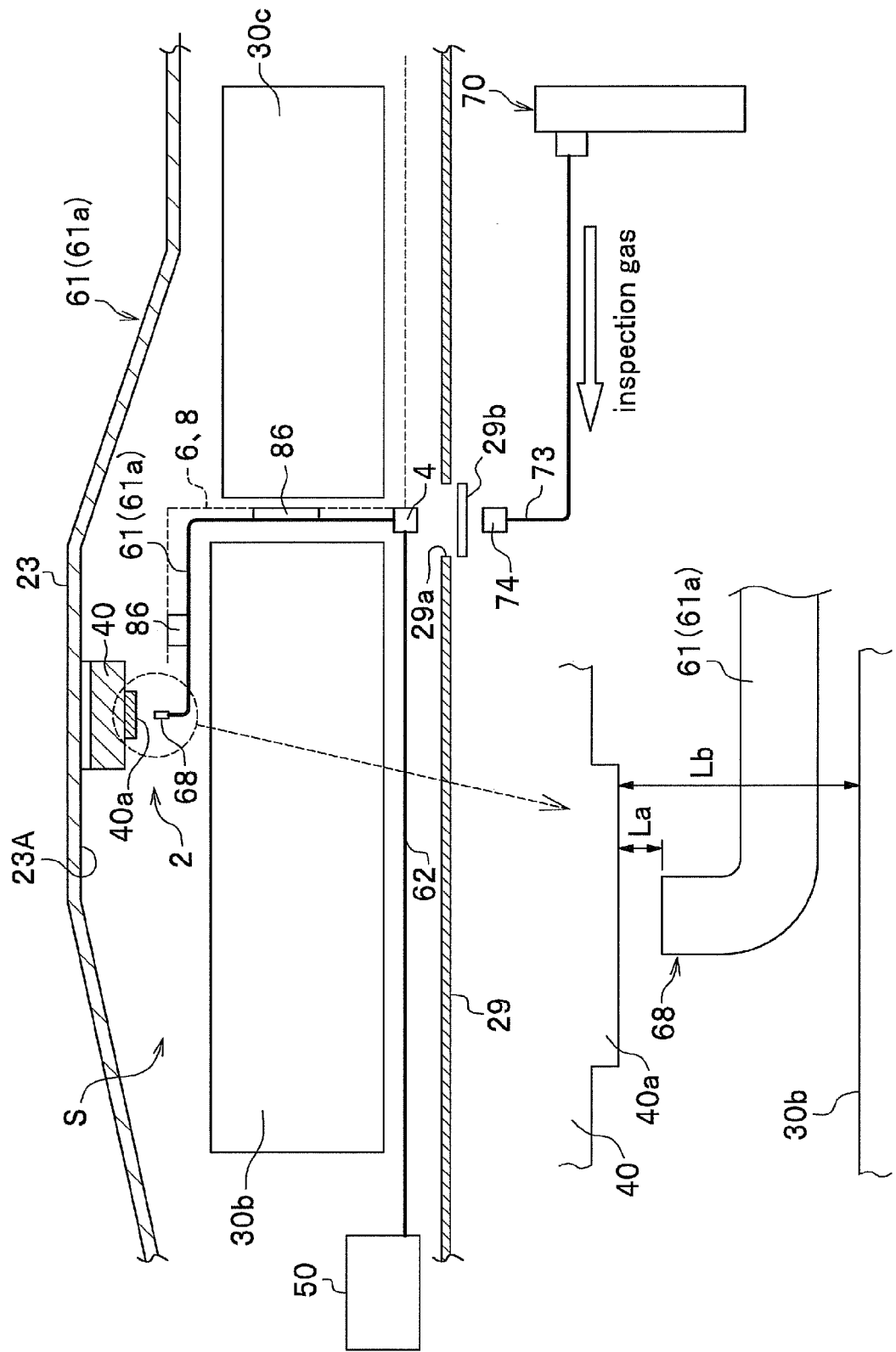
FIG. 2 is a cross section taken along a line A-A in FIG. 1.

The gas sensors 40 are placed, for example, near an outlet piping (not shown) on a cathode side of the fuel cell, and as shown in FIG. 2, also placed in a center tunnel S formed by protruding a center portion of a floor panel 23 of the vehicle 10 toward a vehicle interior side. Specifically, each gas sensing part 40a of the gas sensor 40 faces the corresponding fuel cell device (30a, 30b, 30c, . . . ) such as a fuel tank placed outside the vehicle interior vertically below the floor panel 23 between the floor panel 23 and a lower part 29 of the vehicle body, so that the gas sensors 40 can detect hydrogen gas staying, if any, in a space (fuel gas holding portion) near a lower face 23A of the floor panel 23 forming the center tunnel S. In this manner, even if the fuel gas leaks from the fuel cell or fuel tank, the leaked fuel gas tends to stay in the fuel gas holding portion, and fuel gas leakage can be detected by the gas sensor 40 at an early stage.

It should be noted that in the case of the catalytic combustion type gas sensor 40, the gas sensing part 40a is formed of a sensing element and a temperature compensation element both placed in a gas inspection chamber with an opening.

In addition, the fuel cell system 30 has an inspection gas supply mechanism 2 configured to supply an inspection gas to the gas sensing part 40a of the gas sensor 40. The inspection gas supply mechanism 2 is formed of, for example, an inspection gas introduction piping 61, an inspection gas ejection portion 68, a channel switching connection part 4, and piping attachment member 86.

The inspection gas introduction piping 61 is made of metal, e.g., stainless steel, or non-metallic material, e.g., ethylene-propylene rubber and silicon, and is fixed to the fuel cell system main body or vehicle body together with other piping 6 or electric wiring 8 equipped in the fuel cell system 30, by means of the piping attachment member 86 formed of a guide member or a fixing member, e.g., bracket.

With this piping attachment member 86, the piping 6 or the electric wiring 8 other than the inspection gas introduction piping 61 can be attached to the vehicle body or the main body of the fuel cell system. Therefore, as compared with a case where attachment members are provided for each of the piping 6 and the electric wiring 8, the number of parts can be reduced, improving the mountability of the gas sensor-equipped apparatus 1 to the vehicle body or the like. In addition, the inspection gas introduction piping 61, the piping 6 and the electric wiring 8 can be easily retained in a desired state (e.g., arrangement configuration).

The inspection gas introduction piping 61 may have multiply-branched piping 61a for the respective gas sensors 40, each end of the branched piping 61a being provided with the inspection gas ejection portion 68.

The inspection gas introduction piping 61 is configured to be connected to an external inspection gas supply unit 70 or to an appropriate ventilation-requiring device 50, through the channel switching connection part 4. The term "ventilation-requiring device" herein means a device that requires ventilation from a viewpoint of structure and function, and examples of the ventilation-requiring device 50 include electric power devices, such as a power management and control unit and a battery. Each of these electric power devices is encased in a sealed container (case) in order to protect from intrusion of foreign matters, and also has a vent hole in order to prevent inner pressure fluctuation (air expansion and contraction) that may be caused by heat generation.

Figure 3:
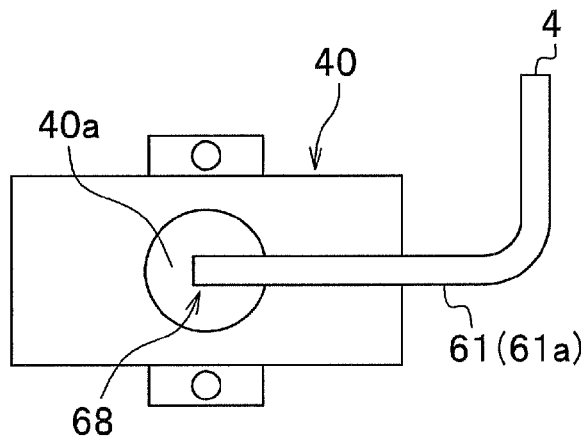
FIG. 3 is a plan view showing a main portion of an inspection gas ejection portion and a gas sensor according to the first embodiment of the present invention seen from below the vehicle body.
Figure 4:
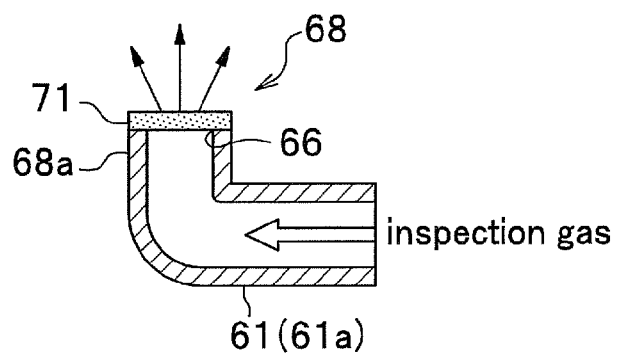
FIG. 4 is a cross section of a main part of an inspection gas ejection portion according to the first embodiment of the present invention.

The inspection gas ejection portion 68 is, for example as shown in FIGS. 2 and 3, disposed on an end portion of the inspection gas introduction piping 61 or the branched piping 61a branched from the inspection gas introduction piping 61 so as to correspond to each of the gas sensors 40. The inspection gas ejection portion 68 has: a curved portion 68a which is bent from the end portion of the inspection gas introduction piping 61 or branched piping 61a towards the gas sensing part 40a of the gas sensor 40; and a nozzle 66 which faces the gas sensing part 40a of the gas sensor 40 with a predetermined ejection clearance La, and has an approximate circular opening from which the inspection gas (flowing through the inspection gas introduction piping 61 or branched piping 61a and then through the curved portion 68a) is sprayed to the gas sensing part 40a, for example in a direction orthogonal to a detection face of the gas sensing part 40a. The nozzle 66 has a water-repellent filter 71 made of, for example, resin.

It should be noted that the outer diameter of the inspection gas introduction piping 61 and the outer diameter of the inspection gas ejection portion 68 is set in such a manner that, for example, a flow space with a specific size required for retaining a desired flow condition is ensured relative to the inspection gas for the gas sensor 40, and specifically a predetermined space clearance including the ejection clearance La is secured in a distance Lb between the gas sensing part 40a of the gas sensor 40 and the fuel cell device 30a facing the gas sensing part 40a.

The value of the ejection clearance La is set in such a manner that, when an inspection gas with a predetermined concentration is sprayed from the nozzle 66, a detection concentration becomes a predetermined stable state within detection accuracy of the gas sensor 40, and the value may be, for example, 5 mm or the like, in the case of the hydrogen gas.

Figure 5A:
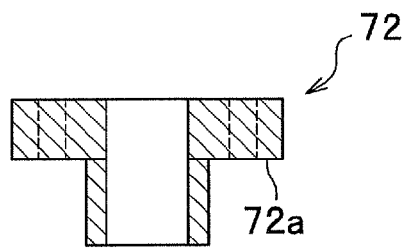
FIG. 5A is a cross section of a main portion of a fastening part of a channel switching connection part according to the first embodiment of the present invention.
Figure 5B:
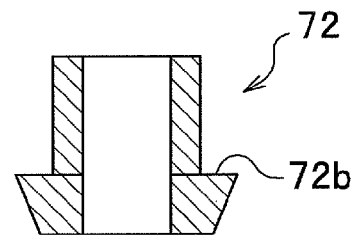
FIG. 5B is a cross section of a main portion of a fastening part of a channel switching connection part according to the first embodiment of the present invention.

The channel switching connection part 4 has a fastening part 72 configured to switch the connection from the inspection gas introduction piping 61, to between an inspection gas supply piping 73 extending from the external inspection gas supply unit 70 and the ventilating piping 62 connected to the ventilation-requiring device 50. The fastening part 72 may have, for example as shown in FIG. 5A, a flange portion 72a or thread portion made of metal, or for example as shown in FIG. 5B, a bulge portion 72b made of a non-metallic material. With this structure, specifically with a fastening member, such as bolt attached to the flange portion 72a of the fastening part 72, or the bulge portion 72b of the fastening part 72, while securing a desired sealing property, the connection of the channel switching connection part 4 can be switched between the inspection gas supply piping 73 and the ventilating piping 62.

When the inspection gas introduction piping 61 and the inspection gas supply piping 73 are connected by the channel switching connection part 4, an inspection gas supplied from the inspection gas supply unit 70 is introduced to the inspection gas introduction piping 61.

When the inspection gas introduction piping 61 and the ventilating piping 62 are connected by the channel switching connection part 4, an appropriate ventilation-requiring device 50 is ventilated through the inspection gas introduction piping 61 and ventilating piping 62.

On an end portion of the inspection gas supply piping 73 of the inspection gas supply unit 70, there is provided a supply-side fastening part 74 configured to be fastened to the fastening part 72 of the channel switching connection part 4. The supply-side fastening part 74 can be inserted into the vehicle body through a through-hole 29a formed in the lower part 29 of the vehicle body, with the through-hole 29a being closable with, for example, a removable cover 29b.

As described above, in the gas sensor-equipped apparatus 1 according to the present embodiment, to the gas sensor 4 placed at a position where no direct visual checking is possible, the inspection gas introduction piping 61 and inspection gas ejection portion 68 capable of supplying the inspection gas are provided. In addition, the inspection gas introduction piping 61 can be connected to the inspection gas supply piping 73 extending from the external inspection gas supply unit 70, through the through-hole 29a formed in the lower part 29 of the vehicle body and closable with the removable cover 29b. As a result, the gas sensor 40 is inspected easily and accurately, while the system structure is prevented from becoming complicated and larger.

In this manner, the inspection gas introduction piping 61 can be connected to the ventilating piping 62 by the channel switching connection part 4, and at least a portion of the inspection gas introduction piping 61 serves as ventilating piping for ventilating the fuel cell system 30. As a result, as compared with a case where piping specially designed for ventilation is provided separately from the inspection gas introduction piping, the system structure is prevented from becoming complicated and larger.

In addition, since the inspection gas ejection portion 68 is provided corresponding to each of a plurality of the gas sensors 40, the inspection gas can be supplied at the same time to the plurality of the gas sensors 40.

<Modified Version>

Figure 6:
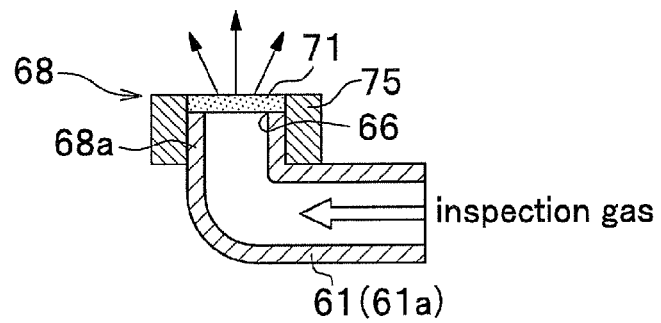
FIG. 6 is a cross section of a main portion of an inspection gas ejection portion according to a modified version of the first embodiment of the present invention.

In the embodiment described above, the water-repellent filter 71 is disposed on the nozzle 66 of the inspection gas ejection portion 68, but for example, as shown in FIG. 6, there may be used a filter cap 75 having the water-repellent filter 71 which is detachably attached to the inspection gas ejection portion 68.

Alternatively, in the above-mentioned embodiment, instead of the water-repellent filter 71, a mesh-like or porous filter made of metal or ceramic may be used.

Figure 7:
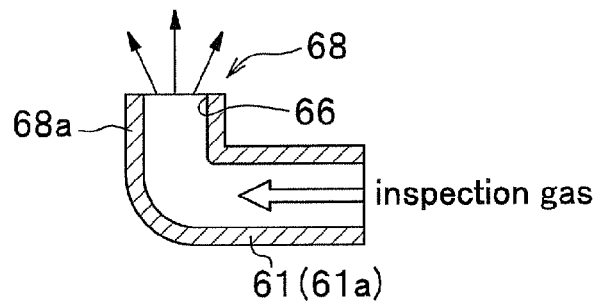
FIG. 7 is a cross section of a main portion of an inspection gas ejection portion according to a modified version of the first embodiment of the present invention.

Alternatively, in the above-mentioned embodiment, the water-repellent filter 71 may be omitted, as shown in FIG. 7.

Figure 8:
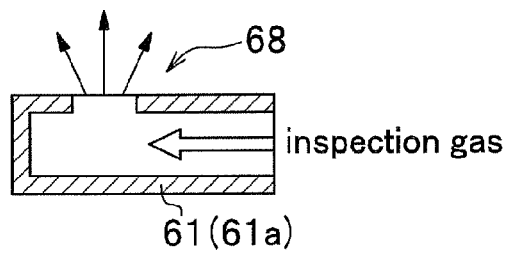
FIG. 8 is a cross section of a main portion of an inspection gas ejection portion according to a modified version of the first embodiment of the present invention.
Figure 9:
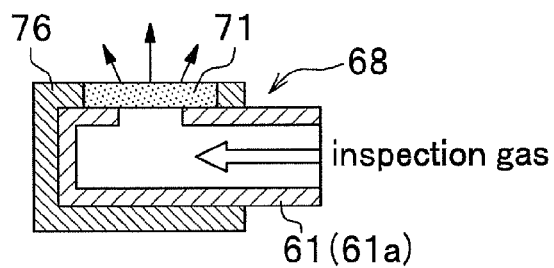
FIG. 9 is a cross section of a main portion of an inspection gas ejection portion according to a modified version of the first embodiment of the present invention.

In the embodiment described above, the inspection gas ejection portion 68 has the curved portion 68a and the nozzle 66, but for example, as shown in FIG. 8, the curved portion 68a may be omitted. In this case, the nozzle 66 may be formed at an appropriate position of the inspection gas introduction piping 61 or the branched piping 61a. For example, as shown in FIG. 9, there may be used a filter cap 76 having the water-repellent filter 71 which is detachably attached to the end portion of the inspection gas introduction piping 61 or the branched piping 61a.

Figure 10:
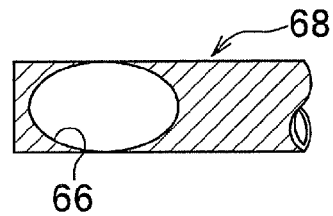
FIG. 10 is a plan view showing a main portion of an inspection gas ejection portion according to a modified version of the first embodiment of the present invention seen from above the vehicle body.
Figure 11:
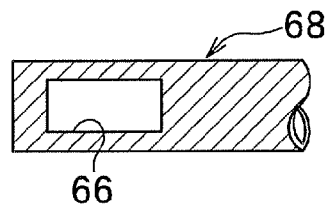
FIG. 11 is a plan view showing a main portion of an inspection gas ejection portion according to a modified version of the first embodiment of the present invention seen from above the vehicle body.

In the embodiment described above, the nozzle 66 of the inspection gas ejection portion 68 has an approximate circular opening, and alternatively, as shown in FIG. 10, it may be in an approximate ellipsoid, or as shown in FIG. 11, an approximate rectangle.

Figure 12:
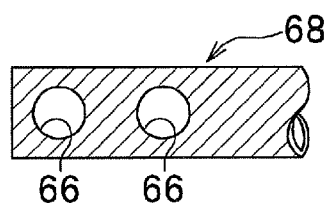
FIG. 12 is a plan view showing a main portion of an inspection gas ejection portion according to a modified version of the first embodiment of the present invention seen from above the vehicle body.
Figure 13:
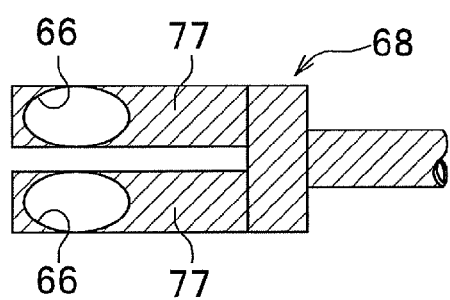
FIG. 13 is a plan view showing a main portion of an inspection gas ejection portion according to a modified version of the first embodiment of the present invention seen from above the vehicle body.

In the embodiment described above, as shown in FIG. 12, the inspection gas ejection portion 68 may have a plurality of nozzles 66 arranged in tandem in a flow direction of the inspection gas, or as shown in FIG. 13, may have multiply-branched ends 77, each branched ends 77 having a single nozzle 66 formed therein.

In the embodiment described above, the piping attachment member 86 may be omitted.

Furthermore, an ECU (Electric Control Unit) configured to control a supercharger, a current controller, an electric storage device and the like as the above-mentioned fuel cell devices 30a, 30b, 30c, . . . may be imparted with a determining function for determining whether or not a failure is present in the gas sensor 40 based on the detection result of the gas sensor 40, and the result may be output to the electric wiring 8 on which a connecting coupler is disposed at the same position as that of the channel switching connection part 4. The inspection gas supply unit 70 may further have a coupler to be connected to the connecting coupler, wiring and a display. With this configuration, work of supplying inspection gas and confirmation of the inspection result (determination) can be done using a single inspection gas supply unit 70 by the same operator at the same location, which enhances efficiency of the inspection work.

In the embodiments described above, the fuel cell system 30 is used as the gas sensor-equipped apparatus 1. Alternatively, the gas sensor-equipped apparatus 1 may be other type of device. Moreover, in the embodiments described above, the vehicle 10 (car) having the fuel cell system 30 mounted thereon has been illustrated. Alternatively, the present invention may be applied to other moving bodies, such as motor cycle, train and ship. Furthermore, the present invention may be applied to a floor type fuel cell system for household or business, a fuel cell system in a hot-water supply system and the like.

Second Embodiment

Next, a second embodiment of the present invention will be described with reference to FIGS. 14 to 17. In the second embodiment, with respect to the gas sensor and piping therefor, a positional relationship in a vehicle body and a relationship with a fuel cell system will be specifically described in more detail.

Figure 14:
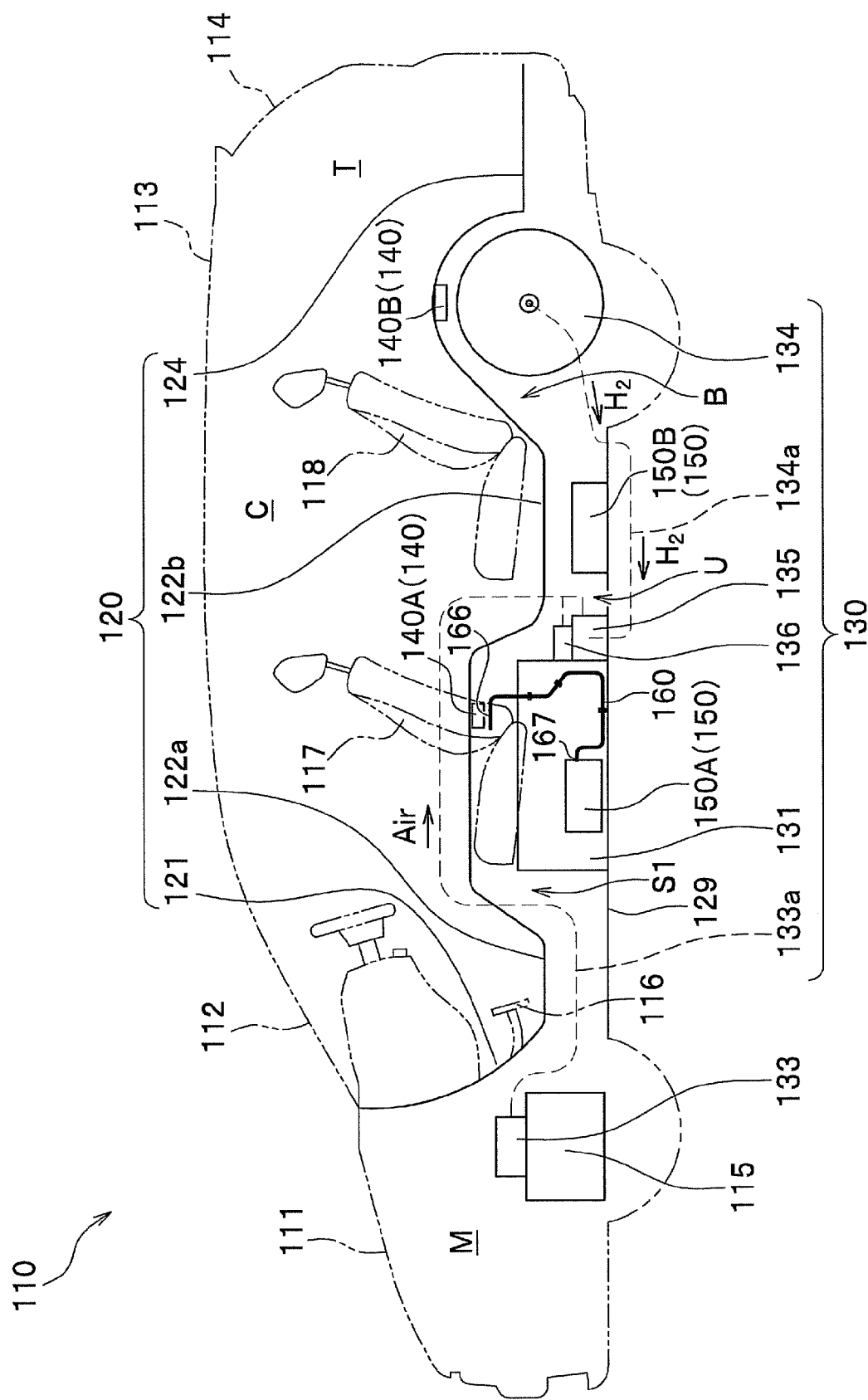
FIG. 14 is a cross section showing a fuel cell vehicle having an apparatus according to a second embodiment of the present invention.

FIG. 14 is a cross section showing a fuel cell vehicle (hereinafter, simply referred to as "vehicle 110") having an apparatus according to the second embodiment.

In the second embodiment, the vehicle 110 has a vehicle interior including a cabin C for crews to be on board, and a trunk room T which is contiguous to the cabin C and capable of storing baggage.

The vehicle interior is defined by a lower panel 120 on a lower side of the vehicle interior, a windshield 112, a roof panel 113, a rear gate 114 and side doors (not shown). On the opposite side of the lower panel 120 to the vehicle interior, a space is formed for disposing main parts of a fuel cell system 130 configured to generate electricity by consuming a fuel gas (hydrogen gas).

The lower panel 120 is contiguously formed of: a dashboard panel 121 comparting a motor room M (defined by a bonnet 111 and a fender panel (not shown)) and the cabin C; a front floor panel 122a having a center tunnel (center console) S1 as a protrusion portion sandwiched between a pair of front seats 117 fixed above the front floor panel 122a; a rear floor panel 122b having a rear sheet 118 fixed thereabove and defining a rear room U therebelow (hereinafter, the front floor panel 122a and the rear floor panel 122b may be collectively referred to as "floor panel 123"); and a trunk floor panel 124 defining a trunk room T thereabove and a tank room B therebelow.

The motor room M, the center tunnel S1, the rear room U and the tank room B, all formed below the lower panel 120, are covered with an under cover 129 at the bottom of the vehicle for protecting the vehicle from splash of mud or flick of stones (chipping) during vehicle running, which provides a contiguous space from a front side to a rear side of the vehicle 110 for disposing the main parts of the fuel cell system 130

On a face of the lower panel 120 facing the fuel cell system 130, a gas sensor 140 (first gas sensor 140A, second gas sensor 140B) configured to detect a leaked fuel gas ($H_2$) is disposed.

The fuel cell system 130 includes: a fuel cell 131 configured to generate power by electrochemical reaction of hydrogen and oxygen and to supply the power to a driving motor 115; an air compressor 133 configured to supply oxygen (air) required for generating power by the fuel cell 131, in accordance with the pressing amount of an accelerator pedal 116; and a fuel tank (fuel gas container, hydrogen tank) 134 configured to compress with high-pressure a fuel gas (H₂) for generating power in the fuel cell 131 and to store the compressed fuel gas therein.

<Fuel Cell>

The fuel cell 131 is a laminated body in a shape of an approximate rectangular parallelepiped, in which a plurality of solid polymer type single cells are stacked in a front-rear direction of the vehicle 110. The fuel cell 131 is fixed onto a sub-frame (not shown) and disposed in the center tunnel S1 under the floor panel 123.

The fuel cell 131 is connected to the air compressor 133 configured to supply air (oxygen), through a cathode auxiliaries 136 and an air supply line 133a; and is connected to the fuel tank 134 configured to supply fuel gas (H₂), through an anode auxiliaries 135 and a fuel supply line 134a.

The fuel cell 131 is configured to generate electricity when current is taken out by appropriately controlling a VCU (Voltage Control Unit) connected to an output terminal of the fuel cell 131, while hydrogen (fuel gas) and air (oxidant gas) are supplied. In other words, the fuel cell 131 (fuel gas container) is in a state of containing hydrogen therein.

The fuel cell 131 is disposed below the first gas sensor 140A and therefore, the first gas sensor 140A cannot be removed without removing the fuel cell 131. In other words, the fuel cell 131 obstructs the exclusive removal of the first gas sensor 140A.

Though the fuel cell 131 is precisely designed and assembled, there remains a possibility that a trace amount of hydrogen and air may leak from fuel cell 131.

When hydrogen leaks from the fuel cell 131, fuel supply line 134a, anode auxiliaries 135 and their connecting portions or other portions, the leaked hydrogen stays in an upper portion (fuel gas holding portion 120a) of the center tunnel S1, due to a small specific gravity of hydrogen. The staying hydrogen is to be detected by the first gas sensor 140A.

<Fuel Tank>

The fuel tank 134 (hydrogen tank) is an approximate column-shaped tank in which hydrogen to be supplied to the fuel cell 131 is stored under high pressure. As shown in FIG. 14, the fuel tank 134 is fixed onto a sub-frame (not shown) by seatings (not shown) arranged on both sides of the fuel tank 134 and is disposed in the tank room B under the floor panel 123. It should be noted that hydrogen in the fuel tank 134 is to be supplied to the fuel cell 131 through an isolation valve, a pressure reducing valve and piping (all not shown).

The fuel tank 134 is disposed below the second gas sensor 140B and therefore, the second gas sensor 140B cannot be removed without removing the fuel tank 134. In other words, the fuel tank 134 obstructs the exclusive removal of the second gas sensor 140B.

Though the fuel tank 134 is precisely designed and has high durability, there remains a possibility that a trace amount of hydrogen may leak from the isolation valve attached to a mouthpiece thereof or the like.

When hydrogen leaks from the fuel tank 134, fuel supply line 134a and their connecting portions or other portions, the leaked hydrogen stays in an upper portion (fuel gas holding portion 120b) of the tank room B, due to a small specific gravity of hydrogen. The staying hydrogen is to be detected by the second gas sensor 140B.

<Cathode Auxiliaries>

The cathode auxiliaries 136 are configured to supply air from the air compressor 133 to the cathode (not shown) of the fuel cell 131, the flow rate of which air is adjusted in accordance with an amount of pressing the accelerator pedal 116 (accelerator opening amount). Examples of the cathode auxiliaries 136 include a humidifier.

The humidifier is configured to humidify air heading for the cathode of the fuel cell 131 from the air compressor 133 in the motor room M through piping, with a humid cathode off-gas discharged from the cathode. The humidifier includes hollow fiber membranes therein for water exchange. As shown in FIG. 14, the humidifier is fixed onto a rear face of the fuel cell 131 and a sub-frame (not shown) and disposed under the floor panel 123.

<Anode Auxiliaries>

The anode auxiliaries 135 are connected to a branched air supply line 133a and provided with a pilot pressure (signal pressure) corresponding to an air flow rate to be supplied to the cathode. The anode auxiliaries 135 are configured to supply a fuel gas (H2) of a flow rate corresponding to the pilot pressure, to the anode (not shown) of the fuel cell 131.

In other words, the anode auxiliaries 135 mechanically adjust a supply pressure of hydrogen based on the pilot pressure (signal pressure), so that a relationship between the hydrogen pressure applied to the anode (not shown) of the fuel cell 131 and the air pressure applied to the cathode becomes constant.

<Electric Power Device>

A power management and control unit 150A is an electric power device 150 that performs a power control in the fuel cell system 130, specifically, a control of supplied power and regenerative power between the fuel cell 131, a high-pressure secondary cell (battery) 150B, a low-pressure secondary power (lead storage battery; not shown) and the driving motor 115. Examples of the power management and control unit 150A include VCU and ECU (Electronic Control Unit).

Specifically, the VCU is a device configured to control generated power (output current, output voltage) of the fuel cell 131 and charge-discharge of the battery 150B, in accordance with a command from the ECU, and has electronic circuits therein, such as DC/DC chopper and DC/DC converter.

As shown in FIG. 14, the power management and control unit 150A is disposed next to the fuel cell 131 in a vehicle width direction and fixed onto a sub-frame (not shown) under the floor panel 123 at a position, for example, below the passenger seat.

A battery 150B is another electric power device 150 that performs a power control in the fuel cell system 130. The battery 150B is configured to charge surplus power of the fuel cell 131 and regenerative power from the driving motor 115, and to discharge charged power to assist the fuel cell 131 during acceleration or the like, and contains therein an assembled battery formed of a plurality of lithium-ion type electric cells (secondary cell) arranged in series. As shown in FIG. 14, the battery 150B is fixed onto a sub-frame (not shown) on a rear side of the fuel cell 131, and disposed under the floor panel 123.

PDU (not shown) is also the electric power device 150 that performs a power control in the fuel cell system 130, and specifically, receives direct-current power in accordance with an opening amount of the accelerator pedal 116 from the power management and control unit 150A, converts the power into three-phase alternating-current power, and outputs the power to the driving motor 115. The PDU (electric power device 150) generates regenerative power during deceleration, and then, in a reverse manner, converts the power into direct-current power, outputs the power to the power management and control unit 150A, and charges the power to the battery 150B.

Since the electric power device 150 has a portion where high output power runs back and forth, the electric power device 150 is encased in a sealed container, in order to prevent internal short-circuit (electrical short) which may otherwise be caused by intrusion of debris, water or the like from outside. In the container forming the sealed space, a vent hole 167 communicating with the atmosphere is formed, in order to prevent inner pressure fluctuation which may be caused along with the generation of Joule heat. To put it another way, the electric power device 150 is a device that requires ventilation of the inside thereof.

From the vent hole 167, a piping system 160 extends, and a nozzle 166 is disposed at an end portion of the piping system 160 and opens toward the gas sensor 140. The piping system 160 is appropriately fixed to peripheral structures, such as the fuel cell 131 and the sub-frame, by brackets.

It should be noted that some possible modified embodiments of the nozzle 166 and surrounding portions thereof has been described in detail in the first embodiment, and thus a duplicate description is omitted.

<Gas Sensor, Inspection Gas Introduction Piping (First Piping)>

The gas sensor 140 is a sensor configured to detect a concentration of the leaked gas (hydrogen), and to output a signal corresponding to the detected concentration to the ECU (not shown). The gas sensor 140 may be, for example, of catalytic combustion type or semiconductor type.

The first piping 161 is configured to lead an inspection gas to the gas sensor 140 during a periodical inspection of the gas sensor 140. The inspection gas is a calibration gas whose hydrogen concentration is adjusted to be a predetermined value, in order to calibrate the gas sensor 140.

The piping system 160 will be described in detail below.

Figure 15A:
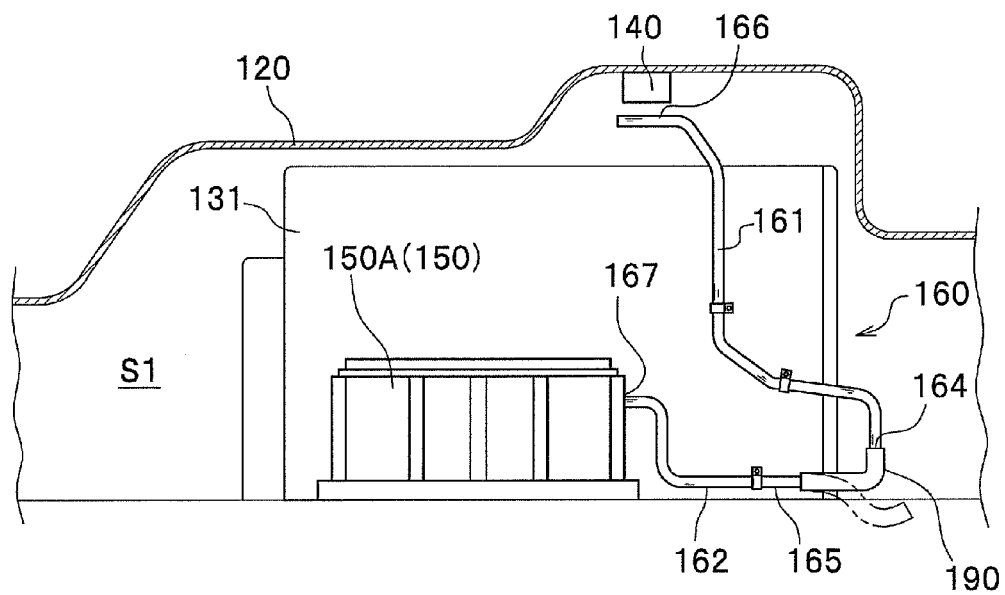
FIG. 15A is a side view showing a piping system (breathing pipe) of an electric power device according to the second embodiment.

FIG. 15A is an enlarged side view showing a portion of the piping system 160 of the power management and control unit 150A (electric power device 150).

The piping system 160 includes: the first piping 161 (inspection gas introduction piping) with one end having the nozzle 166 facing the gas sensor 140 and the other end being a first connecting end 164; a second piping 162 (ventilating piping) having a channel communicating with the inside of the sealed container of the power management and control unit 150A (electric power device 150) and extending from the vent hole 167 to the first connecting end 164 of the first piping 161 through a portion with a level lower than a level of the vent hole 167; and a rubber hose as a connector tube 190 with the ends thereof being detachably connected to the first connecting end 164 and a second connecting end 165. When the gas sensor 140 is inspected, the connector tube 190 is removed to expose the first connecting end 164, and an inspection gas is introduced from the first connecting end 164 to the gas sensor 140.

With this structure of the piping system 160, when the vehicle 110 (see FIG. 14) is in a normal state, the first connecting end 164 and the second connecting end 165 are connected as shown with a solid line. (It should be noted that the expression "normal state" means a state other than the inspection of the gas sensor 140, and thus means a state during an operation of the ventilation-requiring device. Since the ventilation-requiring device and the fuel cell 131 generally interlock, the "normal state" means a state during the electricity generation by the fuel cell 131, in short, a state during the operation of the vehicle 110. Specifically, a normal state includes a state during the operation of the fuel cell 131 and power management and control unit 150A, and during the running and standing of the vehicle 110.) In this case, even when the power management and control unit 150A (electric power device 150) repeats the cycle of normal temperature/heat generation, fresh air enters the sealed space through the nozzle 166 and leaves therefrom, and thus the inner pressure in the sealed container does not fluctuate and intrusion of foreign matters can be prevented. Even when droplets caused by condensation attaches to the inside of the piping system 160 after long-term use, droplets accumulate at the lower portion of the channel than the level of the vent hole 167, and therefore water does not enter the power management and control unit 150A (electric power device 150).

When an amount of the accumulated water is large, the piping system 160 may be clogged and the inner pressure in the sealed container of the power management and control unit 150A cannot be prevented from fluctuating. However, during the periodical inspection of the gas sensor 140, the connecting portion of the first connecting end 164 (or the second connecting end 165) is detached as shown with two-dot chain lines in FIG. 15A, and the accumulated water or the like is discharged. Therefore, even though the inner pressure in the sealed container temporarily fluctuates, serious situation can be prevented.

The gas sensor 140 configured to detect a fuel gas with a small specific gravity is positioned at a high position, and an end of the inspection gas introduction piping (first piping 161) for spraying the inspection gas onto the gas sensing part is also positioned at a high position. Therefore, even when the vehicle 110 runs over a puddle or the like, water barely enters the electric power device 150 through the piping system 160, suitably protecting the electric power device 150.

To put it another way, since the piping system 160 has the above-mentioned features, the first piping 161 configured to inspect the gas sensor 140 can also serve as breathing piping for the power management and control unit 150A (electric power device 150). Moreover, the second piping 162 can be cleaned at the same time as the inspection of the gas sensor 140.

Therefore, by the present invention, the electric power device 150 can be protected from the intrusion of foreign matters, such as water, mud and debris, to thereby securing performance stability, and to provide the fuel cell vehicle 110 having excellent maintainability.

<First Modified Version of Second Embodiment>

Figure 15B:
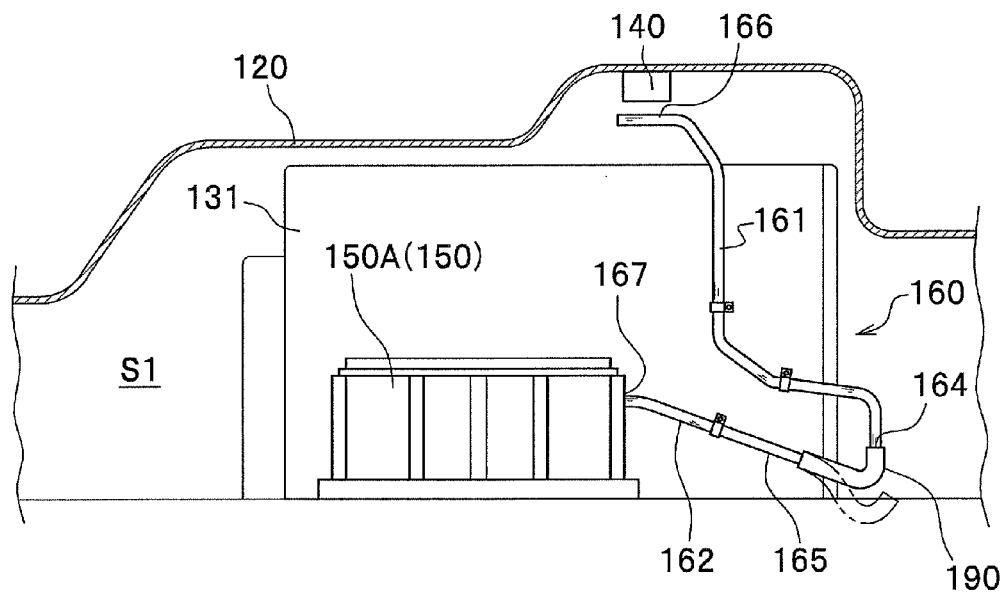
FIG. 15B is a side view showing a modified version of the second embodiment.

FIG. 15B shows a first modified version of the piping system 160.

In this modified version, the second piping 162 includes a downslope portion in the channel from the vent hole 167 to the first connecting end 164 or to the second connecting end 165.

With this structure of the piping system 160, droplets attaching to the inside go down the slope and accumulate at a portion where the piping system 160 is detachably connected. When the connection is detached, water present in the piping system 160 is removed at once.

In the embodiments shown in FIGS. 15A and 15B, the rubber hose which is flexible as a whole and undergoes elastic deformation is illustrated as the connector tube 190, for connecting the first connecting end 164 and the second connecting end 165 brought into a proximity to each other. Alternatively, the connector tube 190 may be bellows made of a metallic tube. The connector tube 190 does not have to have flexibility along its entire length, and only a portion in the vicinity of the portion detachably connected may be imparted with flexibility, while the connector tube 190 is retained long (a distance between the first connecting end 164 and the second connecting end 165 is retained long). Alternatively, only one of the connecting ends of the connector tube 190 may have flexibility.

With this structure, a degree of freedom of the design of the piping system 160 is improved, the detaching and connecting of the piping system 160 upon the inspection of the gas sensor 140 becomes simple, and in a normal state, a portion detachably connected is securely connected, preventing foreign matters from intruding into the piping system 160.

It should be noted that the connector tube 190 is not an essential component, and may not be present if one end portion of either of the first piping 161 or the second piping 162 has a structure that functions as the connector tube 190.

<Second Modified Version of Second Embodiment>

Figure 16:
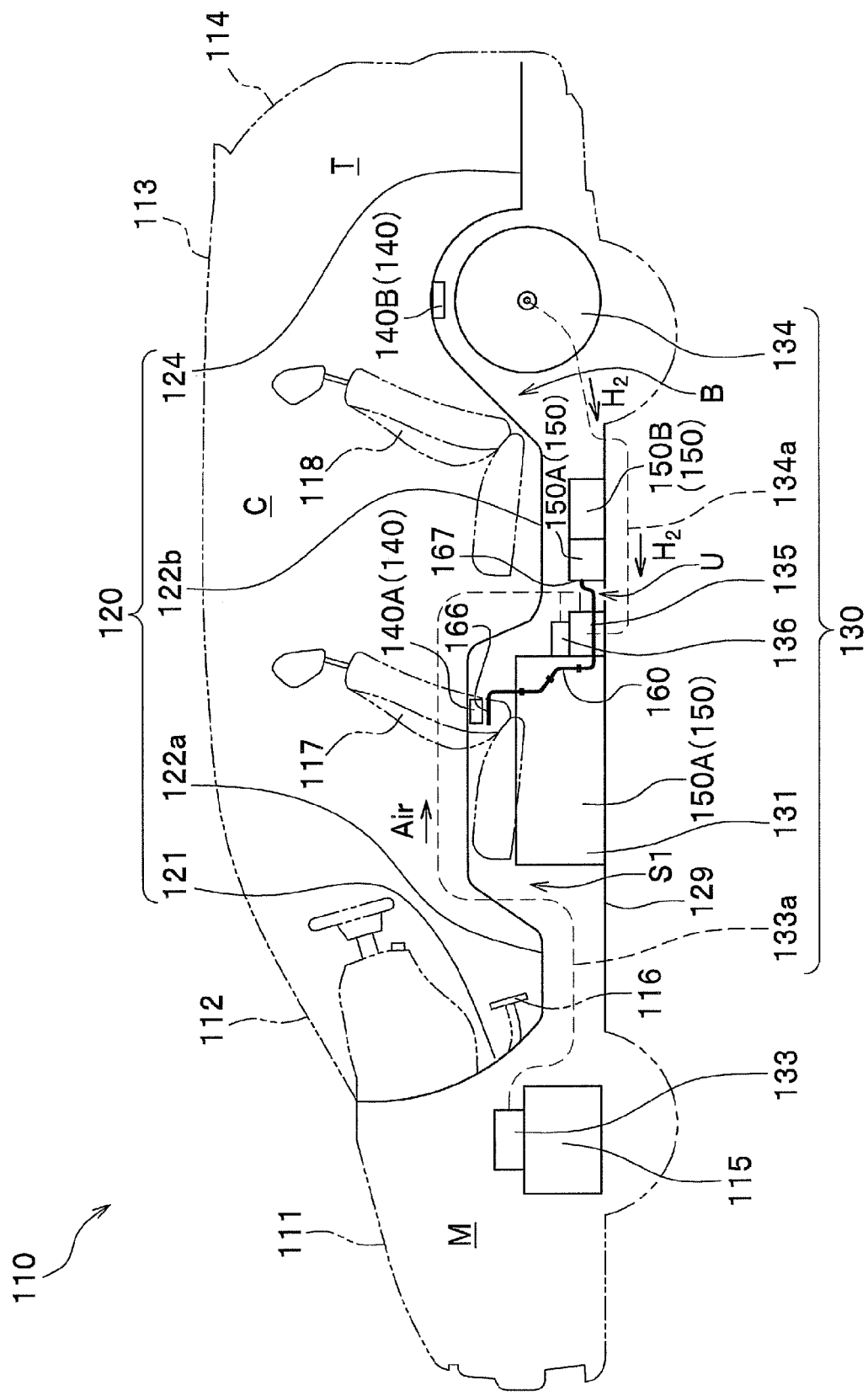
FIG. 16 is a cross section showing a fuel cell vehicle having an apparatus according to a second modified version of the second embodiment of the present invention.

FIG. 16 shows a second modified version of the vehicle 110 having the piping system 160, in which the power management and control unit 150A (electric power device 150) is integrally formed with the battery 150B (electric power device 150) positioned on a rear side.

Also in this case, a channel of the piping system 160 extends from the vent hole 167 and passes a portion lower than the level of the vent hole 167; the end portion of the channel is positioned near the gas sensor 140; and the nozzle 166 is formed in the end portion in such a manner that the nozzle 166 faces the gas sensor 140.

It should be noted that, though it is not shown, the first piping 161 having the nozzle 166 and the second piping 162 extending from the vent hole 167 are detachably connected through the connector tube 190.

<Third Modified Version of Second Embodiment>

Figure 17:
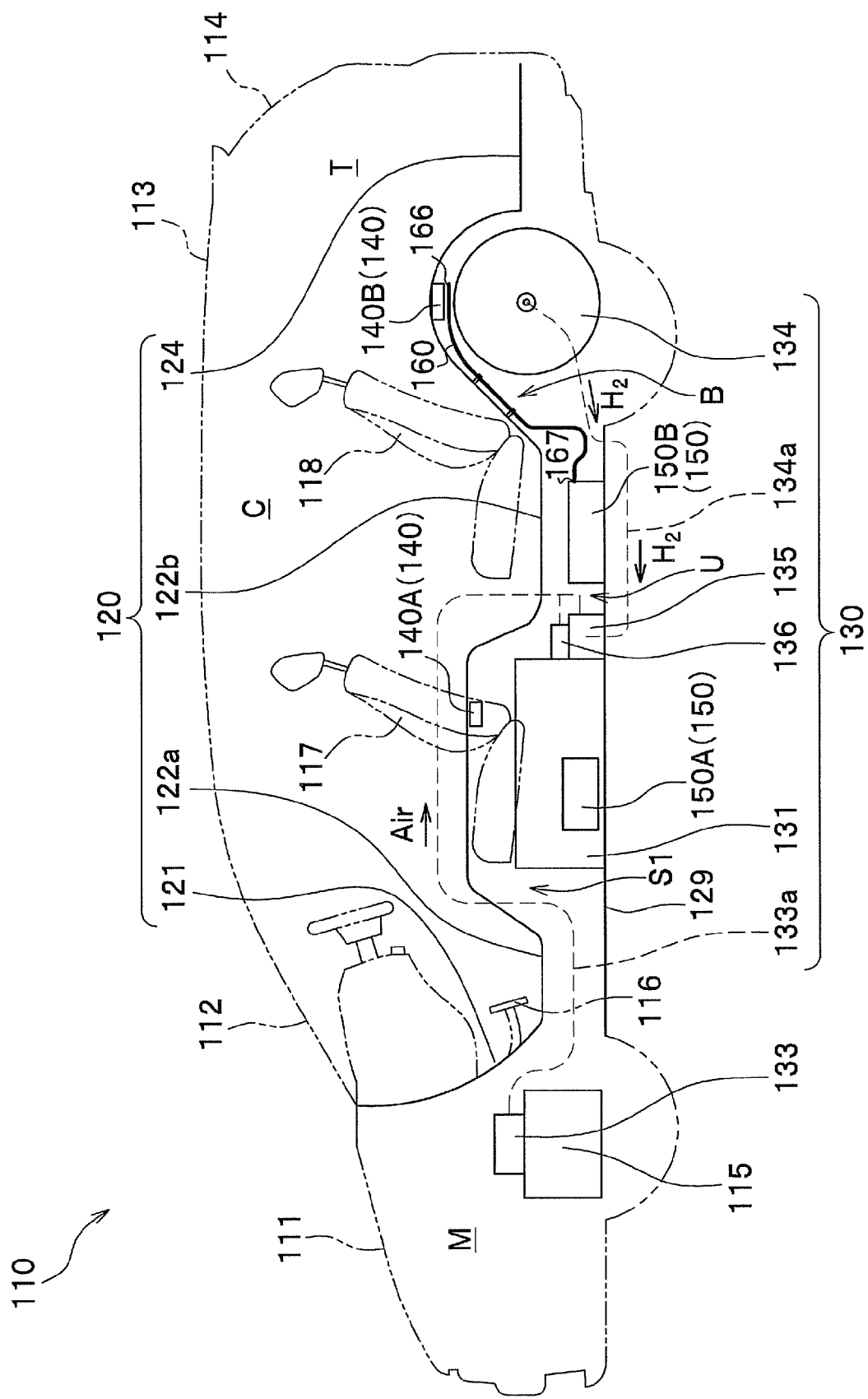
FIG. 17 is a cross section showing a fuel cell vehicle having an apparatus according to a third modified version of the second embodiment of the present invention.

FIG. 17 shows a third modified version of the vehicle 110 in which the inspection gas introduction piping for the second gas sensor 140B (140) positioned near the fuel tank 134 also function as piping communicating with the inside of the electric power device 150 (shown as battery 150B).

Also in this case, a channel of the piping system 160 extends from the vent hole 167 and passes a portion lower than the level of the vent hole 167; the end portion of the channel is positioned near the gas sensor 140; and the nozzle 166 is formed in the end portion in such a manner that the nozzle 166 faces the gas sensor 140.

It should be noted that, though it is not shown, the first piping 161 having the nozzle 166 and the second piping 162 extending from the vent hole 167 are detachably connected through the connector tube 190.

The embodiments of the present invention have been described above. However, the present invention is not limited to the above-described embodiments, and it is a matter of course that the above embodiments may be properly modified.

For example, in the embodiments described above, the vehicle 110 (car) having the fuel cell system 130 mounted thereon has been illustrated. Alternatively, the present invention may be applied to other moving bodies, such as motorcycle, train and ship. Furthermore, the present invention may be applied to a floor type fuel cell system for household or business, a fuel cell system in a hot-water supply system and the like.

Third Embodiment

Next, a third embodiment of the present invention will be described with reference to FIGS. 18 to 22. It should be noted that components in the third embodiment equivalent to the components in the second embodiment with reference numerals in the 100s are numbered with 200s (last two digits are the same), and will be described in detail only when necessary. The components different form those of the second embodiment will be mainly described.

Figure 18:
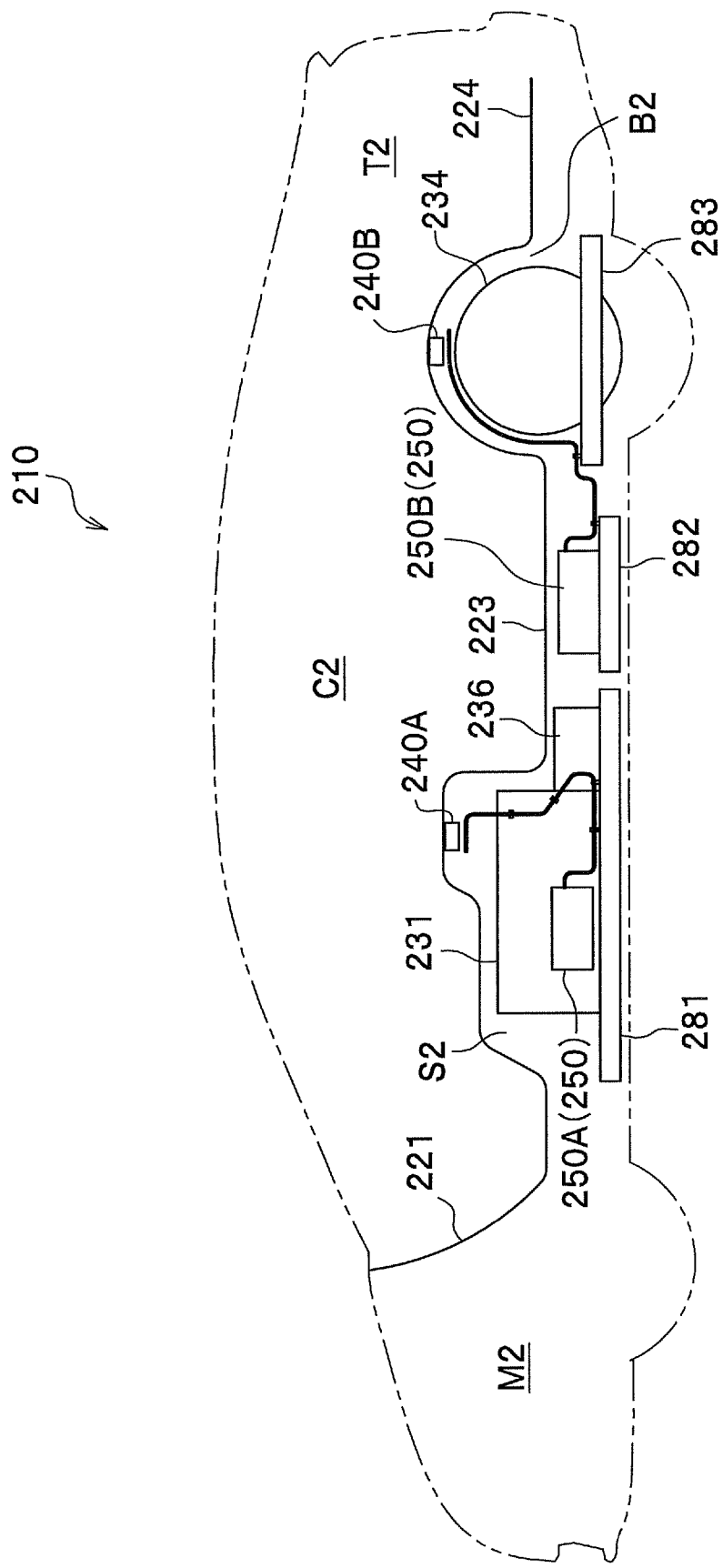
FIG. 18 is a side view showing a fuel cell vehicle having an apparatus according to a third embodiment.

In a vehicle 210 shown in FIG. 18 according to the third embodiment, lattice-wise arranged sub-frames 281, 282, 283 to be installed to a vehicle body, such as side frames, are specifically illustrated. The sub-frames 281, 282, 283 are designed in such a manner that when assembled with the vehicle body including side frames and the like, they come to a predetermined positional relationship with the vehicle body.

<First Gas Sensor 240A and First Piping 261a>

Figure 19:
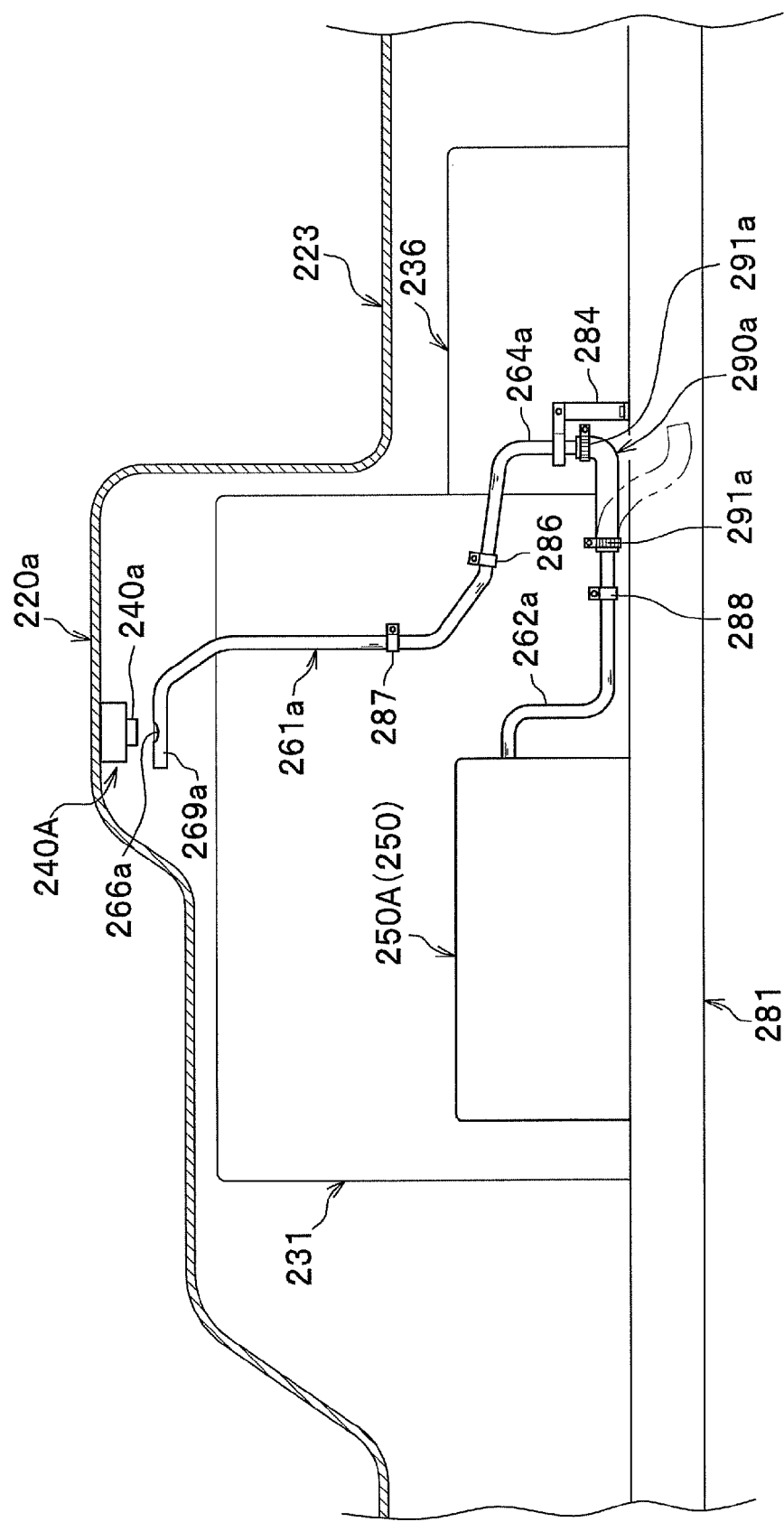
FIG. 19 is a side view showing a fuel cell and surrounding portions according to the third embodiment.
Figure 20:
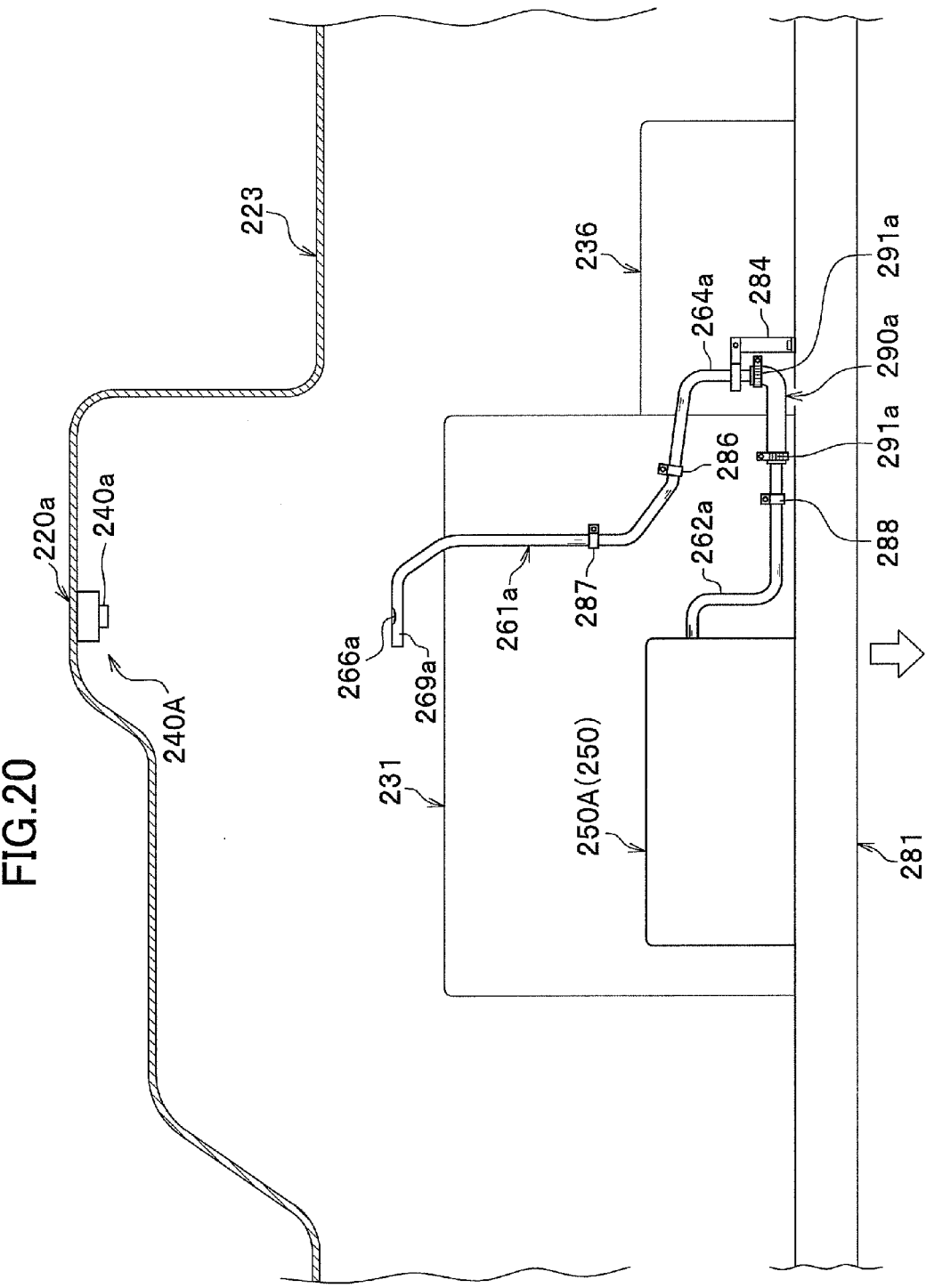
FIG. 20 is a side view showing a state in which the fuel cell according to the third embodiment is removed.

With reference to FIGS. 19 and 20, structures and functional effects of a first gas sensor 240A, a first piping (inspection gas introduction piping) 261a and surrounding portions thereof will be described in detail.

The first gas sensor 240A is configured to detect hydrogen which leaks mainly from a fuel cell (fuel gas container) 231 and stays in a fuel gas holding portion 220a, and removably attached to a lower face of a floor panel 223 forming the fuel gas holding portion 220a above the fuel cell 231, by a bolt or the like. A gas sensing part 240a of the first gas sensor 240A is in an approximate cylindrical shape and has a downward opening, so as to capture hydrogen staying in the fuel gas holding portion 220a. It should be noted that, in the gas sensing part 240a and a gas sensing part 240b, which will be described later, have respective gas sensing elements (not shown) for detecting hydrogen.

The first piping 261a is configured to lead an inspection gas toward the first gas sensor 240A, and spray the inspection gas to the gas sensing part 240a of the first gas sensor 240A from an end 269a side, during a periodical inspection of the first gas sensor 240A. In the first piping 261a on the end 269a side, a nozzle 266a configured to eject the inspection gas is formed so as to face the gas sensing part 240a having a downward opening, and thus the inspection gas is allowed to be sprayed to the gas sensing part 240a.

The first piping 261a is fixed to the sub-frame 281 through a bracket 284, and to the fuel cell 231 through brackets 286, 287. A second piping 262a, which will be described below, is also fixed to the fuel cell 231 through a bracket 288.

In a normal state, a first connecting end 264a of the first piping 261a is connected to the second piping (ventilating piping) 262a through a rubber hose (connector tube) 290a. The first connecting end 264a of the first piping 261a extends to a lower side of the vehicle 210, and accordingly, during the inspection of the first gas sensor 240A, for example, when an under cover (not shown) of the vehicle 210 is removed, the first connecting end 264a is exposed on the lower side of the vehicle.

On connecting portions of the rubber hose 290a with the first piping 261a and with the second piping 262a, hose bands 291a, 291a are attached, in order to prevent the rubber hose 290a from falling off which may otherwise be caused by vibration or the like.

With this structure, in the normal state, the inside of a power management and control unit 250A (electric power device 250) communicates with a center tunnel S2 through the second piping 262a, the rubber hose 290a, the first piping 261a and the nozzle 266a, with the nozzle 266a serving as a ventilating hole. Therefore, the power management and control unit 250A in which air expands or contracts due to the operation of the power management and control unit 250A is ventilated through the second piping 262a, the first piping 261a and the like. In addition, since the nozzle 266a functioning as a ventilating hole is positioned above the power management and control unit 250A, even when, for example, the vehicle 210 runs over a puddle, water is prevented from entering the power management and control unit 250A.

<Procedure for Installing First Piping 261a>

Herein, procedure for installing the first piping 261a will be described.

At a predetermined position of the sub-frame 281 before being installed to the vehicle body, the fuel cell 231 and cathode auxiliaries 236 are fixed. The sub-frame 281 is configured so as to be in predetermined positional relationships with the vehicle body and with the first gas sensor 240A fixed thereto, when installed to the vehicle body. Therefore, the bracket 284 fixed to the sub-frame 281 is also brought into a predetermined positional relationship with the first gas sensor 240A, when the sub-frame 281 is installed to the vehicle body.

In addition, the attachment position of the first piping 261a to the bracket 284 is designed, using an engineering drawing, in such a manner that the inspection gas from the nozzle 266a is directed toward the gas sensing part 240a. It should be noted that the attachment position of the first piping 261a is marked, for example, with positioning pins, and this attachment position and the bracket 284 form a positioning mechanism for setting the first piping 261a to the predetermined position relative to the sub-frame 281.

First, the first piping 261a is attached to the bracket 284 fixed to the sub-frame 281, while performing a position adjustment, and then attached to the brackets 286, 287 fixed to the fuel cell 231. Subsequently, the sub-frame 281 to which the fuel cell 231, the cathode auxiliaries 236 and the first piping 261a are attached is raised with a hydraulic jack or the like, to thereby install the sub-frame 281 to the vehicle body. As a result, the nozzle 266a is positioned so as to face the opening of the gas sensing part 240a.

In this manner, the first piping 261a is positioned not relative to the brackets 286, 287 fixed to the fuel cell 231, but to the bracket 284 fixed to the sub-frame 281, and thus the first piping 261a can be precisely installed. With this structure, when the first gas sensor 240A is inspected, the inspection gas from the nozzle 266a can be suitably sprayed to the gas sensing part 240a of the first gas sensor 240A, and needless spraying of the inspection gas can be prevented.

<Inspection of First Gas Sensor 240A>

Next, the inspection of the first gas sensor 240A will be described.

First the under cover of the vehicle 210 is removed, and then the rubber hose 290a on a first piping 261a side is detached. Subsequently, an inspection gas is introduced to the first connecting end 264a of the first piping 261a. The inspection gas is then led to the first gas sensor 240A through the first piping 261a, and appropriately sprayed from the nozzle 266a on the end 269a side of the first piping 261a to the gas sensing part 240a of the first gas sensor 240A, without needless spray loss. With this structure, the first gas sensor 240A can be suitably inspected.

<Removal of First Gas Sensor 240A>

Next, removal of the first gas sensor 240A will be described when an extensive examination or the like is required based on the result of the inspection, such as the first gas sensor 240A as determined to be out of order.

After removing the under cover of the jacked-up vehicle 210, while supporting the sub-frame 281 with a hydraulic jack or the like, the sub-frame 281 is detached from the vehicle body. Subsequently, the sub-frame 281 is lowered by the hydraulic jack or the like (see FIG. 20).

As a result, the fuel cell 231, power management and control unit 250A and first piping 261a fixed onto the sub-frame 281 are also lowered together with the sub-frame 281, and the first gas sensor 240A is exposed downward. In this state, the first gas sensor 240A can be easily removed from the floor panel 223.

To put it another way, in a case where the first piping 261a is attached to a floor panel 223 side, after the sub-frame 281 and the fuel cell 231 or the like fixed thereto are removed, it is necessary to remove the first piping 261a, which will complicate the removal step. However, according to the vehicle 210 of the third embodiment, since the first piping 261a is attached to the sub-frame 281 side, when the sub-frame 281 and the fuel cell 231 or the like fixed thereto are removed, the first piping 261a is also removed together, simplifying the removal step. As a result, the first gas sensor 240A can be swiftly removed, improving workability. Moreover, after removing the fuel cell 231 and the first gas piping 261a, the first gas sensor 240A can be visually inspected.

<Second Gas Sensor 240B and First Piping 261b>

Figure 21:
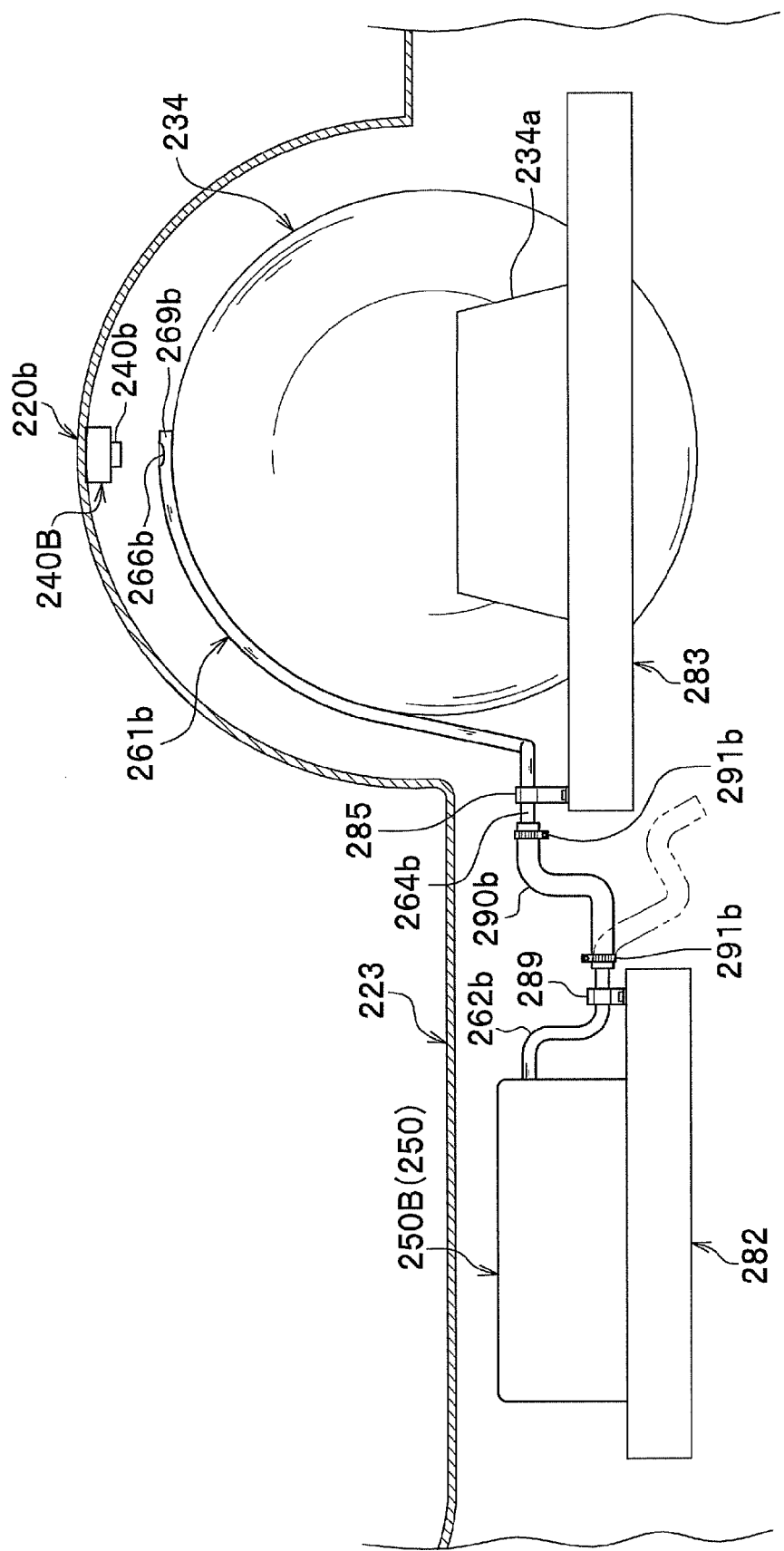
FIG. 21 is a side view showing a fuel tank and surrounding portions according to the third embodiment.
Figure 22:
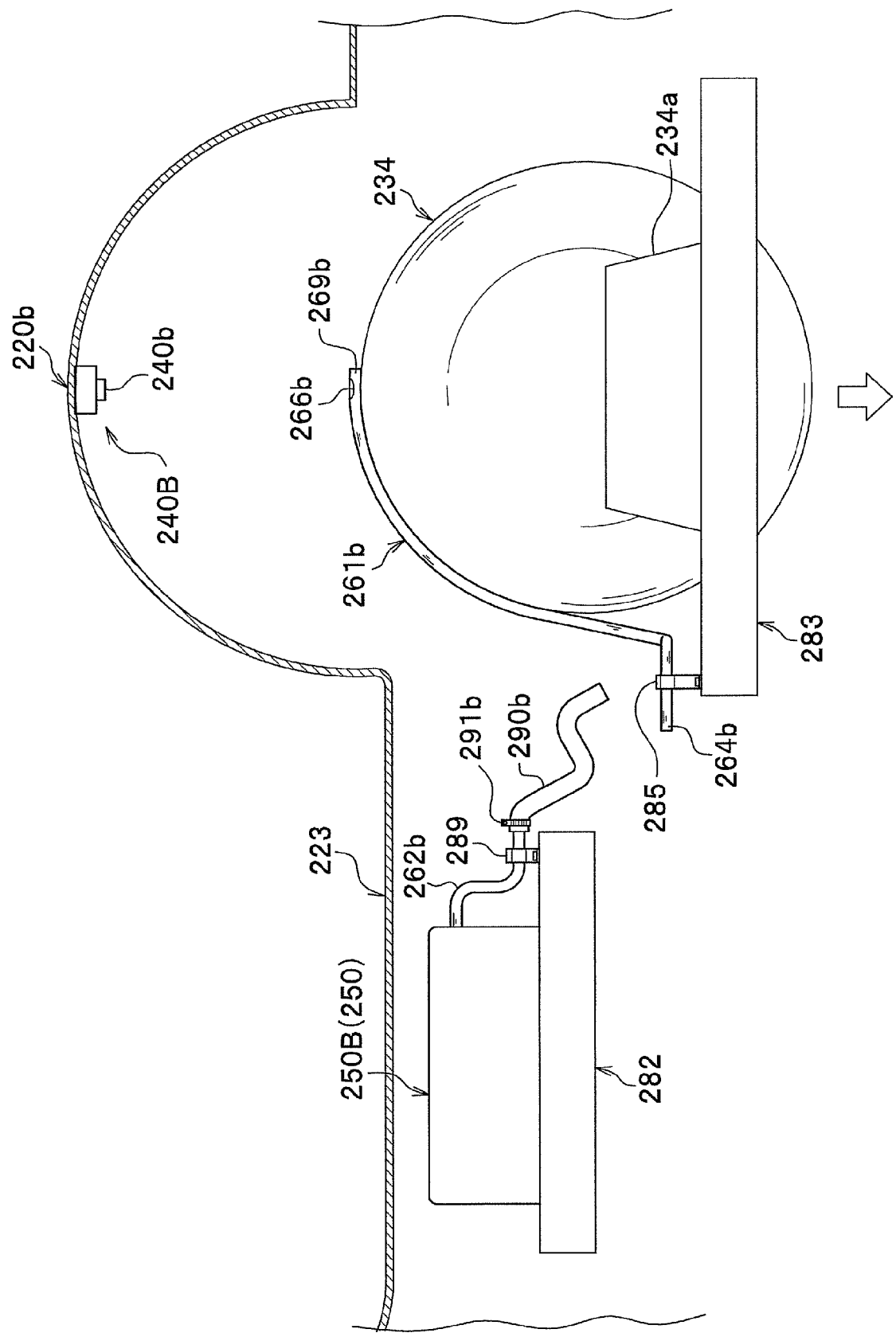
FIG. 22 is a side view showing a state in which the fuel tank according to the third embodiment is removed.

With reference to FIGS. 21 and 22, structures and functional effects of a second gas sensor 240B, a first piping (inspection gas introduction piping) 261b and surrounding portions thereof will be described in detail.

The second gas sensor 240B is configured to detect hydrogen which leaks mainly from a fuel tank 234 and stays in a fuel gas holding portion 220b, and removably attached to the lower face of the floor panel 223 forming the fuel gas holding portion 220b above the fuel tank 234, by a bolt or the like. The gas sensing part 240b of the second gas sensor 240B is in an approximate cylindrical shape and has a downward opening, so as to capture hydrogen staying in the fuel gas holding portion 220b.

The first piping 261b is configured to lead the inspection gas toward the second gas sensor 240B, and sprays the inspection gas to the gas sensing part 240b of the second gas sensor 240B from an end 269b side, during a periodical inspection of the second gas sensor 240B. In the first piping 261b on the end 269b side, a nozzle 266b configured to eject the inspection gas is formed so as to face a gas sensing part 240b having a downward opening, and thus the inspection gas is allowed to be sprayed to the gas sensing part 240b.

The first piping 261b is fixed to the sub-frame 283 through a bracket 285, and to the fuel tank 234 by an adhesive, such as epoxy resin adhesive. A second piping 262b, which will be described below, is fixed to the sub-frame 282 through a bracket 289.

In a normal state, a first connecting end 264b of the first piping 261b is connected to the second piping (ventilating piping) 262b through a rubber hose 290b. The first connecting end 264b of the first piping 261b extends to a lower side of the vehicle 210, and accordingly, during the inspection of the second gas sensor 240B, for example, when an under cover (not shown) of the vehicle 210 is removed, the first connecting end 264b is exposed on the lower side of the vehicle.

On connecting portions of the rubber hose 290b with the first piping 261b and with the second piping 262b, hose bands 291b, 291b are attached, in order to prevent the rubber hose 290b from falling off which may otherwise be caused by vibration or the like.

With this structure, in the normal state, the inside of a battery 250B (electric power device 250) communicates with a tank room B2 through the second piping 262b, the rubber hose 290b, the first piping 261b and the nozzle 266b, with the nozzle 266b serving as a ventilating hole. Therefore, the battery 250B in which air expands or contracts due to the operation of the battery 250B is ventilated through the second piping 262b, the first piping 261b and the like. In addition, since the nozzle 266b functioning as a ventilating hole is positioned above the battery 250B, even when, for example, the vehicle 210 runs over a puddle, water is prevented from entering the battery 250B.

<Procedure for Installing First Piping 261b>

Herein, procedure for installing the first piping 261b will be described.

At a predetermined position of the sub-frame 283 before being installed to the vehicle body, the fuel tank 234 is fixed. The sub-frame 283 is configured so as to be in predetermined positional relationships with the vehicle body and with the second gas sensor 240B fixed thereto, when installed to the vehicle body. Therefore, the bracket 285 fixed to the sub-frame 283 is also brought into a predetermined positional relationship with the second gas sensor 240B, when the sub-frame 283 is installed to the vehicle body.

In addition, the attachment position of the first piping 261b to the bracket 285 is designed, using an engineering drawing, in such a manner that the inspection gas from the nozzle 266b is directed toward the gas sensing part 240b. It should be noted that the attachment position of the first piping 261b is marked, for example, with positioning pins, and this attachment position and the bracket 285 form a positioning mechanism for setting the first piping 261b to the predetermined position relative to the sub-frame 283.

First, the first piping 261b is attached to the bracket 285 fixed to the sub-frame 283, while performing a position adjustment, and then attached to the fuel tank 234 with an adhesive or the like. Subsequently, the sub-frame 283 to which the fuel tank 234 and the first piping 261b are attached is raised with a hydraulic jack or the like, to thereby install the sub-frame 283 to the vehicle body. As a result, the nozzle 266b is positioned so as to face the opening of the gas sensing part 240b.

In this manner, the first piping 261b is positioned not relative to the fuel tank 234 with which it is difficult to perform a positional adjustment due to a curved outer face thereof, but to the bracket 285 fixed to the sub-frame 283, and thus the first piping 261b can be precisely installed. With this structure, when the second gas sensor 240B is inspected, the inspection gas from the nozzle 266b can be suitably sprayed to the gas sensing part 240b of the second gas sensor 240B, and needless spraying of the inspection gas can be prevented.

<Inspection of Second Gas Sensor 240B>

Next, the inspection of the second gas sensor 240B will be described.

First the under cover of the vehicle 210 is removed, and then the rubber hose 290b on a first piping 261b side is detached. Subsequently, an inspection gas is introduced to the first connecting end 264b of the first piping 261b. The inspection gas is then led to the second gas sensor 240B through the first piping 261b, and appropriately sprayed from the nozzle 266b on the end 269b side of the first piping 261b to the gas sensing part 240b of the second gas sensor 240B, without needless spray loss. With this structure, the second gas sensor 240B can be suitably inspected.

<Removal of Second Gas Sensor 240B>

Next, removal of the second gas sensor 240B will be described when an extensive examination or the like is required based on the result of the inspection, such as the second gas sensor 240B as determined to be out of order.

After removing the under cover of the jacked-up vehicle 210, the rubber hose 290b on a first piping 261b side is detached, to disconnect the first piping 261b and the battery 250B. In other words, the rubber hose 290b, the hose bands 291b and the like together serve as a detaching mechanism for disconnecting the first piping 261b and the battery 250B, upon removal of the fuel tank 234. In this manner, the first piping 261b and the battery 250B are disconnected, and therefore, there is no need to remove the battery 250B (sub-frame 282) during the removal of the fuel tank 234.

Then, while supporting the sub-frame 283 with a hydraulic jack or the like, the sub-frame 283 is detached from the vehicle body. Subsequently, the sub-frame 283 is lowered by the hydraulic jack or the like (see FIG. 22).

As a result, the fuel tank 234 and first piping 261b fixed onto the sub-frame 283 are also lowered together with the sub-frame 283, and the second gas sensor 240B is exposed downward. In this state, the second gas sensor 240B can be easily removed from the floor panel 223.

To put it another way, since the first piping 261b is attached to the sub-frame 283 side, when the sub-frame 283 and the fuel tank 234 or the like fixed thereto are removed, the first piping 261b is also removed together, simplifying the removal step, and improving workability.

<Modified Version of Third Embodiment>

Figure 23:
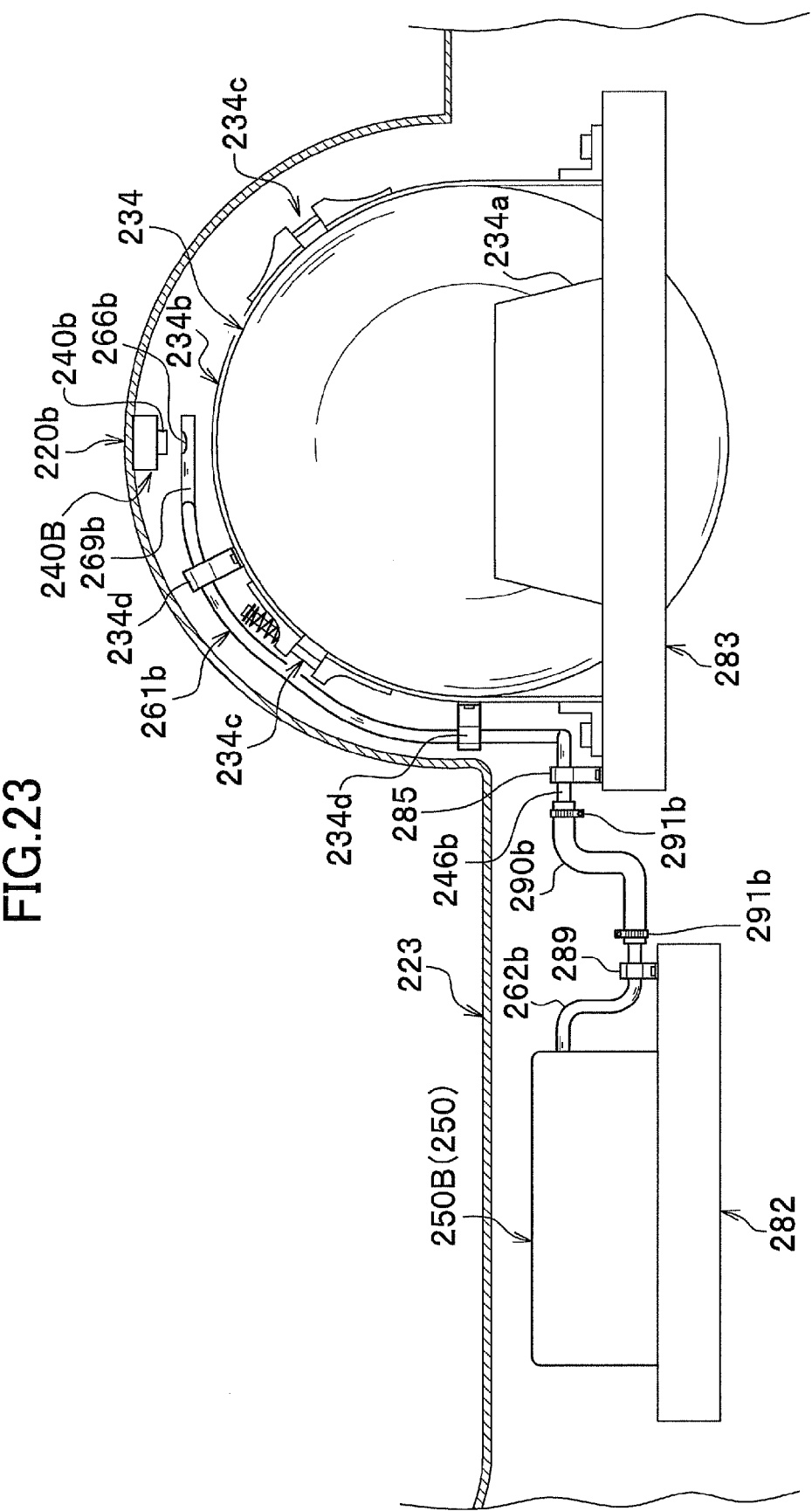
FIG. 23 is a side view showing a fuel tank and surrounding portions according to a modified version of the third embodiment.

Next, a modified version of the third embodiment of the present invention will be described with reference to FIGS. 23 and 24. Descriptions will be made only for the portions different from the third embodiment.

In the modified version, the fuel tank 234 is fixed to the sub-frame 283 through seatings 234a, 234a, and also through two tank bands 234b provided along a periphery of the fuel tank 234. Each tank band 234b is divided into three pieces in a circumferential direction and the pieces are connected to each other with connection jigs 234c, 234c capable of finely adjusting a whole length of the tank band 234b. With this structure, the precise position of the fuel tank 234 is further maintained against vibrations.

In addition, in this modified version, the first piping 261b is not directly fixed to the fuel tank 234 but to brackets 234d, 234d fixed to the tank band 234b. However, a rubber hose 290b side (first connecting end 264b side) of the first piping 261b is attached to the sub-frame 283 through the bracket 285, like in the third embodiment.

The embodiments of the present invention have been described above. However, the present invention is not limited to the above-described embodiments, and it is a matter of course that the above embodiments may be further properly modified.

For example, in the embodiments described above, hydrogen is used as the fuel gas, and alternatively, any fuel gas can be used as long as it generates proton (hydrogen ion) by electrode reaction in the fuel cell and has a smaller specific gravity than that of nitrogen. Examples include methane.

In the embodiments described above, the fuel cell 231, the fuel tank 234 and the battery 250B are separately fixed to the sub-frames 281, 282 and 283, respectively. Alternatively, these components may be fixed onto a single sub-frame, in other words, they may share a sub-frame.

What is claimed is:

1. A fuel cell system, comprising:
a fuel cell configured to generate electricity with a fuel gas and an oxidant gas supplied thereto,
a fuel gas container configured to contain a fuel gas therein,
an electric power device configured to perform a power control of the fuel cell system and encased in a sealed container having a vent hole,
a fuel gas holding portion configured to surround an upper portion of the fuel gas container,
a gas sensor configured to detect a specific gas which is a subject for detection and comprising a gas sensing part having a downward opening, configured to be installed in the fuel gas holding portion and to detect a fuel gas staying in the fuel gas holding portion,
first piping configured to lead an inspection gas to the gas sensor and to spray the inspection gas onto the gas sensing part from an end portion of the first piping, and
second piping which comprises a channel communicating with the sealed container and extending from the vent hole,
wherein at least a portion of the first piping connected to the second piping serves as ventilating piping for the electric power device.

2. The fuel cell system according to claim 1, wherein the channel of the second piping extending from the vent hole is detachably connected to the first piping.

3. The fuel cell system according to claim 2, wherein the channel of the second piping extending from the vent hole is detachably connected to the first piping through a portion with a level lower than a level of the vent hole.

4. The fuel cell system according to claim 2 further comprising a connector tube having at least a flexible portion, with the ends of the connector tube being detachably connected to a first connecting end of the first piping and a second connecting end of the second piping.

5. The fuel cell system according to claim 3, wherein the channel of the second piping extending from the vent hole to the portion which is detachably connected to the first piping comprises a downslope.

6. A fuel cell vehicle comprising the fuel cell system according to claim 1.

7. A fuel cell system, comprising:
   a fuel cell configured to generate electricity with a fuel gas and an oxidant gas supplied thereto,
   a fuel gas container configured to contain a fuel gas therein,
   a gas sensor comprising a gas sensing part having a downward opening,
   an inspection gas introduction piping fixed to the fuel gas container and provided separately from the gas sensor, configured to, upon inspecting the gas sensor, lead an inspection gas to the gas sensor and to spray the inspection gas onto the gas sensing part from an end portion of the inspection gas introduction piping,
   a first member, a part of which forms a fuel gas holding portion enclosing an upper portion of the fuel gas container, and
   a second member detachably attached to the first member, wherein the gas sensor is fixed to the fuel gas holding portion and is configured to be installed in the fuel gas holding portion and to detect a fuel gas staying in the fuel gas holding portion, and the fuel gas container is fixed to the second member.

8. The fuel cell system according to claim 7,
   wherein the fuel gas container is a fuel tank configured to store a fuel gas to be supplied to the fuel cell, and
   wherein the fuel cell system further comprises:
      a sub-frame to which the fuel tank is fixed, configured to be brought into a predetermined positional relationship with the gas sensor when installed, and
      a positioning mechanism configured to set the inspection gas introduction piping to a predetermined position relative to the sub-frame.

9. A fuel cell vehicle comprising the fuel cell system according to claim 7.

10. The fuel cell system according to claim 7, wherein the first member is a floor panel and the second member is a sub-frame.

11. the fuel cell system according to claim 7, wherein a nozzle of the inspection gas introduction piping is formed so as to face the gas sensing part having a downward opening.

12. The fuel cell system according to claim 7,
   wherein at least a portion of the inspection gas introducing piping serves as ventilating piping configured to ventilate an inside of a ventilation-requiring device, and
   wherein the ventilation-requiring device is an electric power device.

13. The fuel cell system according to claim 12, wherein the electric power device is a power management and control unit.

14. The fuel cell system according to claim 12, wherein the electric power device is a battery.

* * * * *